US012635877B2

(12) United States Patent
Ma et al.

(10) Patent No.: US 12,635,877 B2
(45) Date of Patent: May 26, 2026

(54) METHODS AND SYSTEMS FOR QUANTIFYING RETINAL VASCULAR PATTERNS AND TREATMENT OF DISEASE

(71) Applicant: Ohio State Innovation Foundation, Columbus, OH (US)

(72) Inventors: Yanhui Ma, Columbus, OH (US); Matthew Ohr, Columbus, OH (US); Cynthia Roberts, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 724 days.

(21) Appl. No.: 17/959,127

(22) Filed: Oct. 3, 2022

(65) Prior Publication Data

US 2023/0346216 A1 Nov. 2, 2023

Related U.S. Application Data

(60) Provisional application No. 63/336,002, filed on Apr. 28, 2022.

(51) Int. Cl.
| | |
|---|---|
| *G16H 20/40* | (2018.01) |
| *A61B 3/10* | (2006.01) |
| *A61B 3/12* | (2006.01) |
| *G06T 7/00* | (2017.01) |
| *G16H 10/60* | (2018.01) |
| *G16H 50/20* | (2018.01) |

(52) U.S. Cl.
CPC ............ *A61B 3/1241* (2013.01); *A61B 3/102* (2013.01); *G06T 7/0012* (2013.01); *G16H 10/60* (2018.01); *G16H 20/40* (2018.01); *G16H 50/20* (2018.01); *G06T 2207/10101* (2013.01); *G06T 2207/30041* (2013.01)

(58) Field of Classification Search
CPC ...... A61B 3/102; A61B 3/1241; G16H 10/60; G16H 15/00; G16H 20/40; G16H 30/40; G16H 50/20; G16H 50/70; G06T 7/0012; G06T 7/13; G06T 7/194; G06T 7/77; G06T 2207/10024; G06T 2207/20081; G06T 2207/30041; G06T 2207/20076; G06T 2207/10101; G06T 2207/20084; G06T 2207/20016; G06T 2207/30101
See application file for complete search history.

(56) References Cited

U.S. PATENT DOCUMENTS

| | | | |
|---|---|---|---|
| 8,879,813 B1 | 11/2014 | Solanki et al. | |
| 2020/0394789 A1 | 12/2020 | Freund et al. | |

FOREIGN PATENT DOCUMENTS

| | | |
|---|---|---|
| WO | 2020/0186222 | 9/2020 |

OTHER PUBLICATIONS

International Search report and Written opinion issued for Application No. PCT/US2022/045573, dated Jan. 30, 2023.
Ma, Y. H. et al. Quantifying the pattern of retinal vascular orientation in diabetic retinopathy using optical coherence tomography angiography. Sci. Rep. 11, 15826 (2021).

(Continued)

*Primary Examiner* — Jack Dinh
(74) *Attorney, Agent, or Firm* — Meunier Carlin & Curfman LLP

(57) ABSTRACT

The present disclosure relates to methods and systems for quantifying the vascular pattern using ocular imaging that shows vessel profiles for the detection, prevention, and treatment of diabetic retinopathy and other related ocular vascular diseases.

25 Claims, 23 Drawing Sheets

D First Derivative

(56) References Cited

OTHER PUBLICATIONS

Llanas, Samantha, et al. "Assessing the use of incorrectly scaled optical coherence tomography angiography images in peer-reviewed studies: a systematic review." JAMA ophthalmology 138.1 (2020): 86-94.

Congdon, N. et al. Causes and prevalence of visual impairment among adults in the United States. Arch. Ophthalmol. (Chicago, Ill. 1960) 122, 477-485 (2004).

Resnikoff, S. et al. Global data on visual impairment in the year 2002. Bull. World Health Organ. 82, 844-851 (2004).

Klein, R., Klein, B. E. K., Moss, S. E., Davis, M. D. & DeMets, D. L. The Wisconsin Epidemiologic Study of Diabetic Retinopathy: II. Prevalence and risk of diabetic retinopathy when age at diagnosis is less than 30 years. Arch. Ophthalmol. 102, 520-526 (1984).

Control, D. & Group, C. T. R. The effect of intensive treatment of diabetes on the development and progression of long-term complications in insulin-dependent diabetes mellitus. N. Engl. J. Med. 329, 977-986 (1993).

Cogan, D. G., Toussaint, D. & Kuwabara, T. Retinal vascular patterns: IV. Diabetic retinopathy. Arch. Ophthalmol. 66, 366-378 (1961).

Kohner, E. M. & Henkind, P. Correlation of fluorescein angiogram and retinal digest in diabetic retinopathy. Am. J. Ophthalmol. 69, 403-414 (1970).

Wang, R. K. et al. Three dimensional optical angiography. Opt. Express 15, 4083-4097 (2007).

Wang, R. K., An, L., Francis, P. & Wilson, D. J. Depth-resolved imaging of capillary networks in retina and choroid using ultrahigh sensitive optical microangiography. Opt. Lett. 35, 1467-1469 (2010).

Jia, Y. et al. Split-spectrum amplitude-decorrelation angiography with optical coherence tomography. Opt. Express 20, 4710-4725 (2012).

Jia, Y. et al. Quantitative optical coherence tomography angiography of vascular abnormalities in the living human eye. Proc. Natl. Acad. Sci. 112, E2395-E2402 (2015).

Li, X.-X. et al. A quantitative comparison of five optical coherence tomography angiography systems in clinical performance. Int. J. Ophthalmol. 11, 1784 (2018).

Corvi, F. et al. Reproducibility of vessel density, fractal dimension, and foveal avascular zone using 7 different optical coherence tomography angiography devices. Am. J. Ophthalmol. 186, 25-31 (2018).

Munk, M. R. et al. OCT-angiography: A qualitative and quantitative comparison of 4 OCT-A devices. PLoS One 12, e0177059 (2017).

Hwang, T. S. et al. Optical coherence tomography angiography features of diabetic retinopathy. Retina 35, 2371 (2015).

Ishibazawa, A. et al. Optical coherence tomography angiography in diabetic retinopathy: a prospective pilot study. Am. J. Ophthalmol. 160, 35-44 (2015).

Salz, D. A. et al. Select features of diabetic retinopathy on swept-source optical coherence tomographic angiography compared with fluorescein angiography and normal eyes. JAMA Ophthalmol. 134, 644-650 (2016).

Schottenhamml, J. et al. An automatic, intercapillary area based algorithm for quantifying diabetes related capillary dropout using OCT angiography. Retina 36, S93 (2016).

Kim, A. Y. et al. Quantifying microvascular density and morphology in diabetic retinopathy using spectral-domain optical coherence tomography angiography. Invest. Ophthalmol. Vis. Sci. 57, OCT362--OCT370 (2016).

Agemy, S. A. et al. Retinal vascular perfusion density mapping using optical coherence tomography angiography in normals and diabetic retinopathy patients. Retina 35, 2353-2363 (2015).

Ma, Y., Zhu, H., Su, B., Hu, G. & Perks, R. The elasto-plastic behaviour of three-dimensional stochastic fibre networks with cross-linkers. J. Mech. Phys. Solids 110, 155-172 (2018).

Herrmann, H., Pastorelli, E., Kallonen, A. & Suuronen, J.-P. Methods for fibre orientation analysis of X-ray tomography images of steel fibre reinforced concrete (SFRC). J. Mater. Sci. 51, 3772-3783 (2016).

Haralick, R. M. Ridges and valleys on digital images. Comput. vision, Graph. image Process. 22, 28-38 (1983).

Frangi, A. F., Niessen, W. J., Vincken, K. L. & Viergever, M. A. Multiscale vessel enhancement filtering. in International conference on medical image computing and computer-assisted intervention 130-137 (1998).

Chu, Z. et al. Quantitative assessment of the retinal microvasculature using optical coherence tomography angiography. J. Biomed. Opt. 21, 66008 (2016).

Fraz, M. M. et al. Blood vessel segmentation methodologies in retinal images—a survey. Comput. Methods Programs Biomed. 108, 407-433 (2012).

Florack, L. M. J., ter Haar Romeny, B. M., Koenderink, J. J. & Viergever, M. A. Scale and the differential structure of images. Image Vis. Comput. 10, 376-388 (1992).

Sato, Y. et al. Three-dimensional multi-scale line filter for segmentation and visualization of curvilinear structures in medical images. Med. Image Anal. 2, 143-168 (1998).

Lorenz, C., Carlsen, I.-C., Buzug, T. M., Fassnacht, C. & Weese, J. Multi-scale line segmentation with automatic estimation of width, contrast and tangential direction in 2D and 3D medical images. in CVRMed-MRCAS'97 233-242 (1997).

Zhang, M. et al. Projection-resolved optical coherence tomographic angiography. Biomed. Opt. Express 7, 816-828 (2016).

Zhang, A., Zhang, Q. & Wang, R. K. Minimizing projection artifacts for accurate presentation of choroidal neovascularization in OCT micro-angiography. Biomed. Opt. Express 6, 4130-4143 (2015).

Otsu, N. A threshold selection method from gray-level histograms. IEEE Trans. Syst. Man. Cybern. 9, 62-66 (1979).

Cunha-Vaz, J., Ribeiro, L. & Lobo, C. Phenotypes and biomarkers of diabetic retinopathy. Prog. Retin. Eye Res. 41, 90-111 (2014).

Hwang, T. S. et al. Automated quantification of capillary nonperfusion using optical coherence tomography angiography in diabetic retinopathy. JAMA Ophthalmol. 134, 367-373 (2016).

Lee, M.-W., Kim, K.-M., Lim, H.-B., Jo, Y.-J. & Kim, J.-Y. Repeatability of vessel density measurements using optical coherence tomography angiography in retinal diseases. Br. J. Ophthalmol. 103, 704-710 (2019).

Liu, Y. et al. Morphological changes in and quantitative analysis of macular retinal microvasculature by optical coherence tomography angiography in hypertensive retinopathy. Hypertens. Res. 44, 325-336 (2021).

Holló, G. Vessel density calculated from OCT angiography in 3 peripapillary sectors in normal, ocular hypertensive, and glaucoma eyes. Eur. J. Ophthalmol. 26, e42-e45 (2016).

Chen, S., Moult, E. M., Zangwill, L. M., Weinreb, R. N. & Fujimoto, J. G. Geometric Perfusion Deficits: A Novel OCT Angiography Biomarker for Diabetic Retinopathy Based on Oxygen Diffusion. Am. J. Ophthalmol. 222, 256-270 (2021).

Al-Sheikh, M., Akil, H., Pfau, M. & Sadda, S. R. Swept-source OCT angiography imaging of the foveal avascular zone and macular capillary network density in diabetic retinopathy. Investig. Ophthalmol. \& Vis. Sci. 57, 3907-3913 (2016).

Zahid, S. et al. Fractal dimensional analysis of optical coherence tomography angiography in eyes with diabetic retinopathy. Investig. Ophthalmol. \& Vis. Sci. 57, 4940-4947 (2016).

Grisan, E., Foracchia, M. & Ruggeri, A. A novel method for the automatic grading of retinal vessel tortuosity. IEEE Trans. Med. Imaging 27, 310-319 (2008).

Danuta M. Sampson, et al. Towards standardizing retinal optical coherence tomography angiography: a review. Light: Science & Applications (2022) 11:63.

C     Second Derivative

D     First Derivative

—(B)

A Regional Division

B  TI

E     NI

F     NS

G    SN

H    ST

B

C

A

SVC: Whole

B DVC: Whole

C

D

A SVC: Whole

B DVC: Whole

C  SVC: Inferior-Nasal

D  DVC: Inferior-Nasal

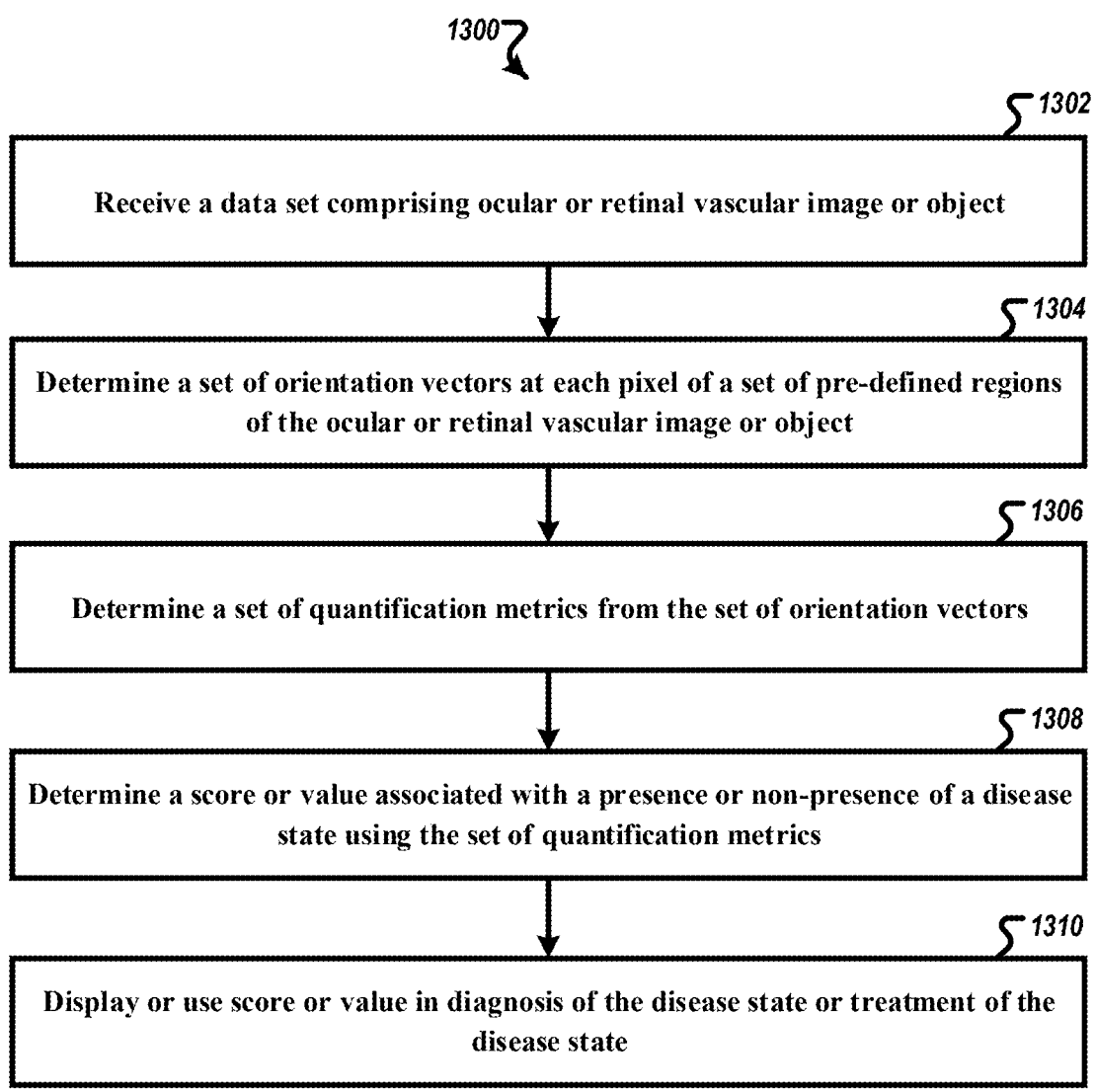

*1300*

*1302*

Receive a data set comprising ocular or retinal vascular image or object

*1304*

Determine a set of orientation vectors at each pixel of a set of pre-defined regions of the ocular or retinal vascular image or object

*1306*

Determine a set of quantification metrics from the set of orientation vectors

*1308*

Determine a score or value associated with a presence or non-presence of a disease state using the set of quantification metrics

*1310*

Display or use score or value in diagnosis of the disease state or treatment of the disease state

FIG. 13

METHODS AND SYSTEMS FOR QUANTIFYING RETINAL VASCULAR PATTERNS AND TREATMENT OF DISEASE

RELATED APPLICATION

This US application claims priority to, and the benefit of, U.S. Provisional Patent Application No. 63/336,002, filed Apr. 28, 2022, entitled "Methods and System for Quantifying Retinal Vascular Patterns and Treating Disease Accordingly," which is incorporated by reference herein in its entirety.

STATEMENT REGARDING FEDERALLY SPONSORED RESEARCH

This invention was made with Government Support under Grant No. R01EY027399 awarded by the National Institutes of Health. The Government has certain right in the invention.

FIELD

The present disclosure relates to methods and systems for retinal vascular imaging as an early biomarker of diabetic retinopathy and other related ocular diseases.

BACKGROUND

Diabetic retinopathy (DR) is the leading cause of vision impairment and blindness among working-age adults in the United States and worldwide, affecting more than three out of 4 individuals with diabetes mellitus of more than 15 years duration. DR is classified into nonproliferative and proliferative stages. Nonproliferative diabetic retinopathy (NPDR) involves progressive intraretinal microvascular alterations that can evolve to a more advanced proliferative stage defined by extraretinal neovascularization impacting both central and peripheral vision. In 1993, the Diabetes Control and Complications Trial (DCCT) demonstrated that intensive metabolic control reduces time-averaged blood glucose values (measured as hemoglobin A1c), and also the incidence and progression of DR. Treatment for DR relies almost exclusively on managing the metabolic dysregulation of diabetes until the severity of vascular lesions, such as clinically significant macular edema or proliferative diabetic retinopathy, warrant prompt treatment. Early detection and timely management of DR can prevent vision loss. In particular, there is a need to identify the retinal dysfunction at the early stage of DR before clinical signs are apparent to result in earlier medical intervention and better visual outcomes for patients.

The compositions, and methods disclosed herein address the need for early detection of diabetic retinopathy.

SUMMARY

The present disclosure provides methods for quantifying the vascular pattern using ocular imaging that shows vessel profiles. A computerized method of the same is disclosed. The computerized method is configured to analyze ocular or retinal vascular image or object to determine vasculature patterns therein. In some embodiments, the analysis determines a set of orientation vectors at each pixel or a set of pixels in a set of pre-defined regions of the ocular or retinal vascular image or object. In some embodiments, Hessian matrix of intensity values of the ocular or retinal vascular image or object is employed. The computerized method can then quantify the orientation vectors that can be outputted in a report to be used in a diagnosis of an ocular or retinal vascular disease. In some embodiments, the orientation vectors are quantified as features for used in trained machine learning classifier, or a training of the same, to provide an indication of a presence or non-presence of the ocular or retinal vascular disease.

In an aspect, a method is disclosed for treating an ocular vascular disease in a patient in need thereof, the method comprising: extracting a retinal vascular feature from an imaging modality obtained from the patient; carrying out a multi-dimensional quantification comprising layer- and sector-based regions of interest (ROIs) to generate a collection of vascular orientation pattern curves; analyzing the vascular orientation pattern curves; placing the patient into a group based on the vascular orientation pattern curve of the patient, wherein said groups comprise: (i) a normal range; (ii) a mildly abnormal range; and (iii) a severely abnormal range. The method further includes selecting the patient from group (ii) for further monitoring and the patient from group (iii) for treatment.

In some embodiments, the ocular vascular disease is a retinal vascular disease.

In some embodiments, the retinal vascular feature comprises one or more features comprising a vessel orientation ranging from 0° to 180°, a retinal sector, or a retinal layer.

In some embodiments, the retinal sector comprises 8 equal sections of a macula.

In some embodiments, the retinal sector comprises at least a temporal-inferior (TI) sector, an inferior-temporal (IT) sector, an inferior-nasal (IN) sector, a nasal-inferior (NI) sector, a nasal-superior (SN) sector, a superior-nasal (SN) sector, a superior-temporal (ST) sector, or a temporal-superior (TS) sector.

In some embodiments, the retinal layer is selected from the group comprising a full-projection layer, a superficial vascular plexus (SVP), an intermediate capillary plexus (ICP), a deep capillary plexus (DCP), a superficial vascular complex (SVC), and a deep vascular complex (DVC).

In some embodiments, the imaging modality comprises optical coherence tomography angiography (OCTA), fluorescein angiography (FA), indocyanine green angiography (ICGA), or color fundus photography.

In some embodiments, the multi-dimensional quantification further comprises a preferred vessel orientation, a vessel anisotropy, and a vessel area.

In some embodiments, the vascular orientation pattern captures local variations in the vessel orientation.

In some embodiments, the vessel of the DR patient aligned between 0°-39° is about 40%-80% different compared to a normal patient in the SVC or the DVC of the IN sector.

In some embodiments, the vessel of the DR patient aligned between 40°-79° is about 25%-40% different compared to a normal patient in the SVC or the DVC of the IN sector.

In some embodiments, the vessel of the DR patient aligned between 80°-119° is about 0%-20% different compared to a normal patient in the SVC or the DVC of the IN sector.

In some embodiments, the vessel of the DR patient aligned between 120°-149° is about 15%-50% different compared to a normal patient in the SVC or the DVC of the IN sector.

In some embodiments, the vessel of the DR patient aligned between 150°-180° is about 40%-80% different compared to a normal patient in the SVC or the DVC of the IN sector.

In some embodiments, the normal range of the DR patient is between 0%-20% different compared to a normal patient.

In some embodiments, the mildly abnormal range of the DR patient is between 20%-40% different compared to a normal patient.

In some embodiments, the severely abnormal range of the DR patient is more than 40% different compared to a normal patient.

In some embodiments, an area under the curve indicates the vessel area density (VAD).

In some embodiments, the retinal vascular disease is selected from any one of the groups consisting of diabetic retinopathy, macular degeneration, retinal vein occlusions, retinopathy of prematurity, retinal artery microaneurysm, hypertension (including hypertensive retinopathy and other hypertension-related diseases such as preeclampsia), atherosclerosis, vasculitis, blood dyscrasia, a systemic infection, radiation exposure, lupus, AIDs, or any other disease associated with retinopathy.

In some embodiments, the patient is being monitored for any one of the above-discussed retinal vascular disease.

In some embodiments, the patient in the treatment range receives a treatment corresponding to the retinal vascular disease.

In some embodiments, the treatment is anti-vascular endothelial growth factors (anti-VEGF), laser, and/or gene therapy.

In another aspect, a method is disclosed for screening an ocular or vascular disease progression in a patient, wherein the disease progression is indicated by a change in a vessel orientation distribution.

In some embodiments, method of screening is performed during an annual eye exam.

In some embodiments, the change in the vessel orientation distribution is a 10% or more increase compared to a normal patient in a SVC or a DVC.

In some embodiments, the disease progression is screened about every 365 days.

In some embodiments, the ocular vascular disease is a retinal vascular disease.

In some embodiments, the retinal vascular disease is selected from any one of the groups consisting of diabetic retinopathy, macular degeneration, retinal vein occlusions, retinopathy of prematurity, retinal artery microaneurysm, hypertension (including hypertensive retinopathy and other hypertension-related diseases such as preeclampsia), atherosclerosis, vasculitis, blood dyscrasia, a systemic infection, radiation exposure, lupus, AIDs, age-related macular degeneration, or any other disease associated with retinopathy.

In another aspect, a computer-executed method is disclosed comprising receiving, by a processor, a data set comprising ocular or retinal vascular image or object; determining, by the processor, a set of orientation vectors at each pixel, or a set of pixels, of a set of pre-defined regions of the ocular or retinal vascular image or object, including a first region and a second region; determining, by the processor, a set of first quantification metrics from the set of orientation vectors for the first region; and determining, by the processor, a set of second quantification metrics from the set of orientation vectors for the second region; wherein the first and second sets of quantification metrics are employed in a diagnosis or a treatment of an ocular or retinal vascular disease.

In some embodiments, the first and second sets of quantification metrics are used by a trained machine learning or neural network to output an indication of a presence or non-presence of the ocular or retinal vascular disease, wherein the trained machine learning or neural network was trained using orientation vectors at each pixel, or the set thereof, of pre-defined regions of a training data set comprising ocular or retinal vascular images or objects and labels for the ocular or retinal vascular disease.

In some embodiments, the set of orientation vectors are determined by generating a Hessian matrix of intensity values of the ocular or retinal vascular image or object and determining eigenvector corresponding to the smallest eigenvalue in magnitude of the Hessian matrix.

In some embodiments, quantification metrics are generated from a set of 8 pre-defined retinal sectors centered at an identified landmark corresponding to the macula.

In some embodiments, the first quantification metrics includes an aggregation or sum of a number of orientation vectors in a pre-defined angle or angular range.

In some embodiments, the ocular or retinal vascular data comprises 2D ocular or retinal vascular data, 3D ocular or retinal vascular data, or time-dependent ocular or retinal vascular data.

In another aspect, a system is disclosed comprising a processor; and a memory having instructions stored thereon, wherein execution of the instructions by the processor causes the processor to perform the computer-executed method of any one of above-discussed methods.

In another aspect, a non-transitory computer-readable medium is disclosed having instructions stored thereon, wherein execution of the instructions by the processor causes the processor to perform any one of the above-discussed computer-executed methods.

BRIEF DESCRIPTION OF FIGURES

The accompanying figures, which are incorporated in and constitute a part of this specification, illustrate several aspects described below.

FIG. 1A shows a gray-scale image of a tube-like structure. FIG. 1B shows an intensity profile of 2-dimensional Gaussian with standard deviation s=1. Zero-crossings of the second derivative shown in FIG. 1C correspond to the local maxima in the first derivative in FIG. 1D.

FIG. 2A shows vessel orientations were calculated by the Hessian matrix-based algorithm. FIG. 2B shows the enlargement of FIG. 2A: the arrows indicate the vessel directions/orientations. Note the algorithm is demonstrated on large vessels for illustration.

FIG. 3A shows the original OCTA image centered at the macula. FIG. 3B shows the region of interest after vesselness filter and binary filter. FIG. 3C shows an orientation map: dark blue and red indicate 0 and 180 degrees for those horizontal vessels and green indicates 90 degrees for those vertical vessels. The image processing was operated on the full thickness (non-segmented) en face OCTA image.

FIG. 4B shows the orientation pattern for the specific region of interest (ROI) in FIG. 4A depicting a roughly elliptical shape with a major axis and a minor axis.

The preferred orientation is identified by the angle of the major axis. The ratio of major axis length and minor axis length is defined as vessel anisotropy. The vessel area is defined as the area of the shape. FIG. 4C shows the examples of preferred orientation, vessel anisotropy, and vessel area, illustrated by the dashed ellipse relative to the solid ellipse.

FIGS. 5A-I shows the eight 45° sectors divided from a circular disk centered at the macula and each sector defined as the region of interest for the quantitative assessment of retinal vascular orientation pattern. N=nasal, S=superior, T=temporal, I=inferior.

FIG. 8A shows the scatterplot of the relationship between vessel area and vessel density in the IT sector. FIG. 8B shows the average of 8 sectors in healthy subjects. The vessel area quantified from the retinal vascular orientation pattern was strongly correlated with the traditionally reported vessel density with Pearson R=0.99 for both IT sector and on average (p<0.0001, n=34).

FIGS. 9A and 9C show whole vs IN in the SVC. FIGS. 9B and 9D show whole vs IN in the DVC.

FIGS. 10A and 10C show vascular orientation pattern curves in whole vs IN in the SVC. FIGS. 10B and 10D show vascular orientation pattern curves in whole vs IN in the DVC.

FIG. 11A shows the percentage difference between NRL and DR in the inferior-nasal sector in the deep vascular complex (DVC) and superficial vascular complex (SVC). FIG. 1B shows a color orientation map for a representative NRL subject and a representative DR patient in DVC and SVC.

FIG. 13 shows an example method of operation of the system of FIG. 12.

DETAILED DESCRIPTION

Figure 1A:
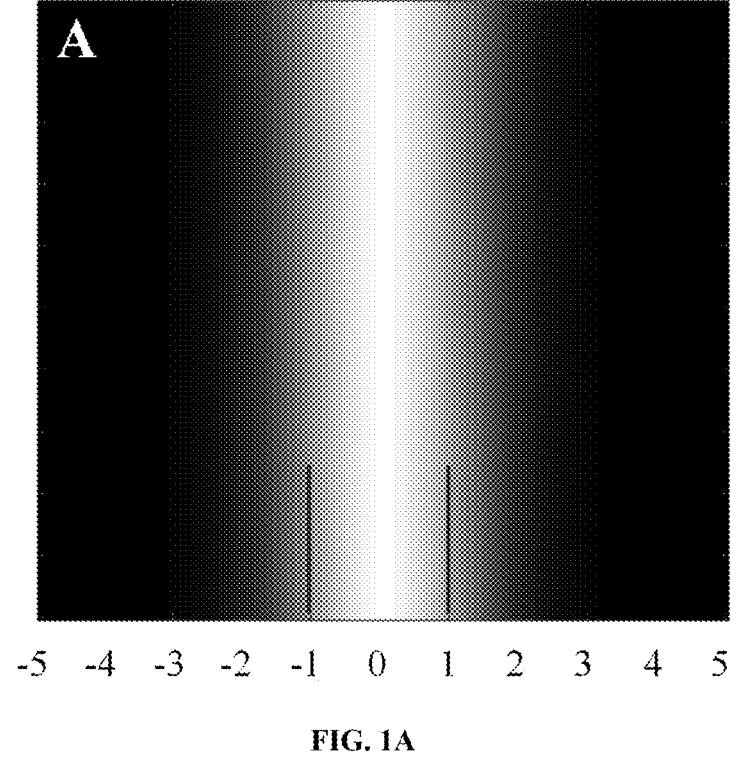
FIGS. 1A, 1B, 1C, and 1D show the second derivative of the intensity in a gray-scale image used as an edge-detection operator.
Figure 1B:
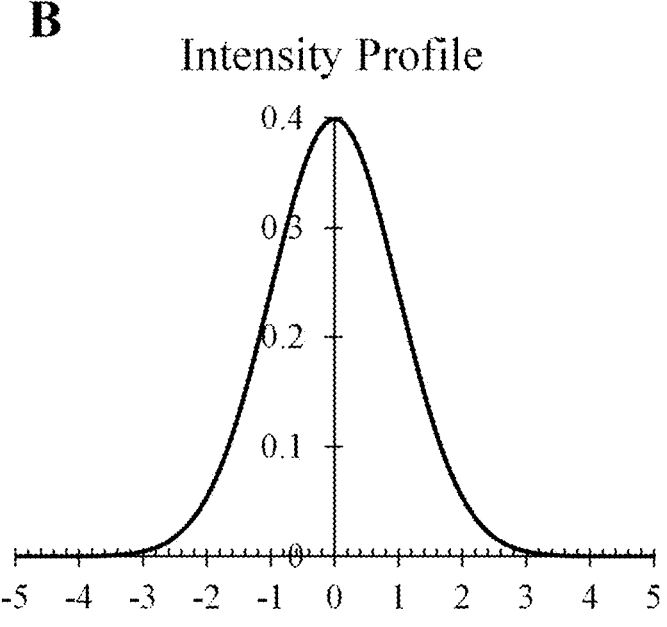
Figure 1C:
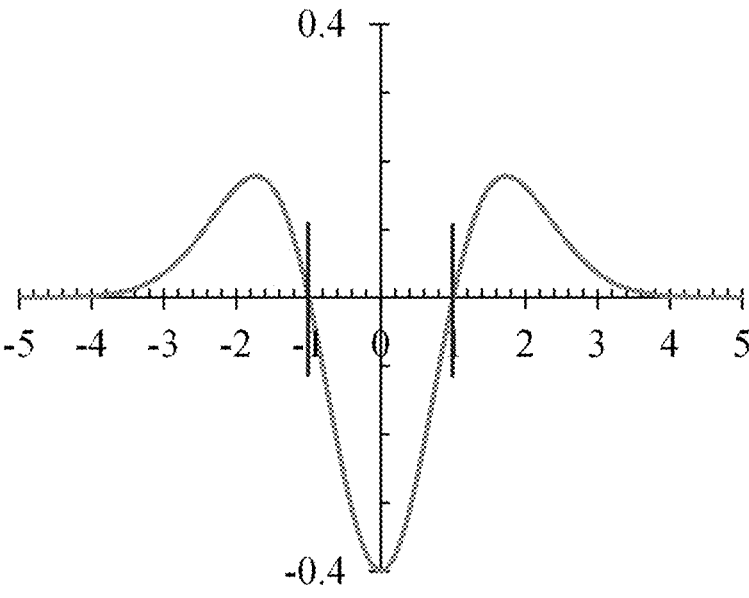
Figure 1D:
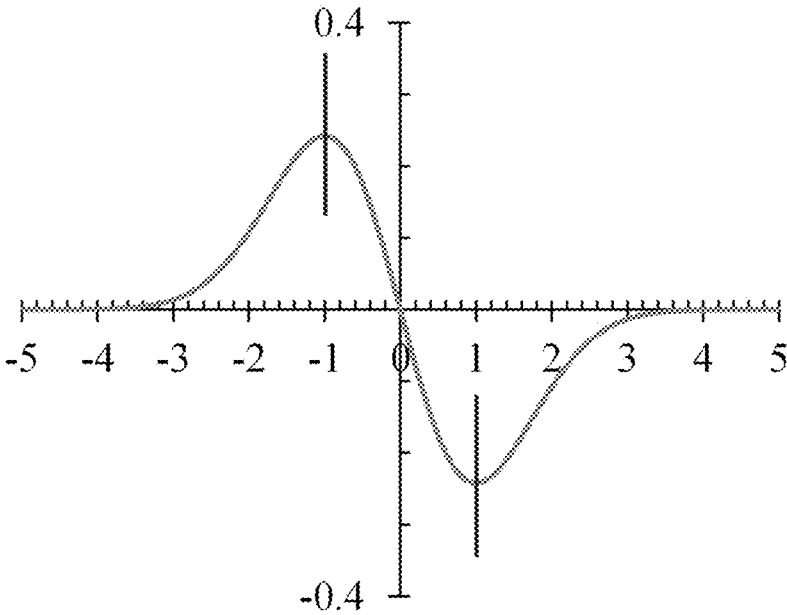

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Reference will now be made in detail to the embodiments of the invention, examples of which are illustrated in the drawings and the examples. This invention may, however, be embodied in many different forms and should not be construed as limited to the embodiments set forth herein.

Terminology

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

The following definitions are provided for the full understanding of terms used in this specification.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

"Composition" refers to any agent that has a beneficial biological effect. Beneficial biological effects include both therapeutic effects, e.g., treatment of a disorder or other undesirable physiological condition, and prophylactic effects, e.g., prevention of a disorder or other undesirable physiological condition. The terms also encompass pharmaceutically acceptable, pharmacologically active derivatives of beneficial agents specifically mentioned herein, including, but not limited to, a vector, polynucleotide, cells, salts, esters, amides, proagents, active metabolites, isomers, fragments, analogs, and the like. When the term "composition" is used, then, or when a particular composition is specifically identified, it is to be understood that the term includes the composition per se as well as pharmaceutically acceptable, pharmacologically active vector, polynucleotide, salts, esters, amides, proagents, conjugates, active metabolites, isomers, fragments, analogs, etc.

An "increase" can refer to any change that results in a greater amount of a symptom, disease, composition, condition or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

The terms "treat," "treating," "treatment," and grammatical variations thereof as used herein, include partially or completely delaying, alleviating, mitigating, or reducing the intensity of one or more attendant symptoms of a disorder or condition and/or alleviating, mitigating, or impeding one or more causes of a disorder or condition. Treatments according to the disclosure may be applied preventively, prophylactically, palliatively, or remedially. Treatments are administered to a patient prior to onset (e.g., before obvious signs of disease) or during early onset (e.g., upon initial signs and symptoms of disease).

The term "detect" or "detecting" refers to signs or symptoms noted in the process of identifying a disease, condition, or injury. For example, vascular orientation pattern curves used herein would detect difference in retinal vasculature in patients with or at risk of retinal vascular diseases.

As used herein, "monitoring", "monitor", or "monitored" refers to the actions of observing and checking the progress or quality of a treatment or procedure over a period of time. "Monitoring" and other variations of the term also refers to observing the course of a disease or condition, such as diabetic retinopathy or macular degeneration, over a period of time.

A "retinal vascular disease" is a condition that affects the blood vessels of the eye that usually causes visual loss without prompt diagnosis and treatment. Common retinal vascular diseases include, but are not limited to diabetic retinopathy, hypertensive retinopathy, retinal vein and/or artery occlusions, and age-related macular degeneration.

A "patient" is any subject receiving or awaiting to receive medical care or treatment. A "patient" can be a human, non-human primate, non-human mammal, or any other vertebrate or non-vertebrate animal. For example, a patient can be a human, a dog, a cat, a monkey, an ape, a bird, a frog, a mouse, a rabbit, a fish, a jellyfish, or snake.

As used herein, "extract", "extracting", "extracted" or any other variations refers to obtaining a resource, substance, or data from an initial source, for example, to include, but not limited to an image, sample, or medical history, wherein the initial source provides further information about the health, condition, and status of a subject or patient.

As used herein, a "feature" refers to a distinctive attribute or aspect of a particular characteristic or component. For example, a layer or sector of the retina is a retinal feature. A preferred vessel orientation in a layer or sector of the retina is a retinal vascular feature.

"Preferred vessel orientation" refers to the property of blood vessels that has a dominant alignment with a certain angle. For instance, measuring the blood vessel at 900 could have the largest amount than blood vessels at any other degree.

"Vessel anisotropy" refers to the property of blood vessels that changes or assumes different properties in different directions. For example, the properties of a blood vessel can change depending on the orientation, or angle, to which it is being measured. For instance, measuring the blood vessel at $0°$ could have different measurements then measuring the blood vessel at $90°$, and the difference (quantified by ratio) could be different among different regions of interest (ROIs) or over time. The measured physical or mechanical properties include, but are not limited to absorbance, refractive index, tensile strength, and elasticity.

"Vessel area" (also referred to as vessel area density) as used herein refers to the proportion of vessel area in the eye/retina with blood flow over the total area measured. The quantitative property can be expressed as a percentage of the ratio of the total area within a region of interest (ROI) relative to the total vessel area.

"Vessel probability" (also referred to as vessel distribution intensity) refers to the amount of pixels belonging to the vessel aligned at a certain angle or range of angles. For instance, the vessel is aligned in different directions, and the vessel probability at x angle ($x∈[0,180°]$) could be different from at y angle ($y∈[0,180°]$). These terms can be used to describe the y-axis, as described in Example 2.

As used herein, a "vessel" refers to tissues that form hollow tubes or a network of tubes through which blood circulates in the body. For example, blood vessels include a network of arteries, arterioles, capillaries, venules, and veins that act to transport blood throughout the body.

As used herein, "orientation" refers to the relative position of an object or structure relative to a particular focal or original point. For example, the angle of a blood vessel ranging from $0°-180°$ is considered to be the vessel orientation.

The "retina" is the innermost, light-sensitive layer of tissue within the eye of most vertebrates, including, but not limited to humans. Retinal tissue comprises several layers made up of light-sensing cells called photoreceptor cells, which detect and process light coming into the retina.

The "macula" refers to an oval-shaped pigmented area in the center of the retina of most vertebrate eyes, including, but not limited to humans. This area of the retina is responsible for producing central, high-resolution color vision. High-resolution color vision is lost when the macula is damaged as a result of macular degeneration.

The "fovea" refers to the more centrally located region within the macula of the retina of most vertebrates, including, but not limited to humans. The fovea is a small, central locus of densely packed photoreceptor cells, called cones, responsible for sharp, central vision.

A "gene therapy" refers to a medical/clinic approach to treat or prevent a disease, condition, or disorder by correcting an underlying genetic issue. This therapeutic technique involves introducing a gene to a subject or patient to replace or alleviate consequences of the dysfunction gene(s) causing the disease, condition, or disorder.

As used herein, "normal" refers to a standard of health where no disease, disorder, abnormal condition, mutation, or dysfunction exists within a particular subject or patient. "Normal" can also refer to an average or typical state or condition. Normal can be defined as not varying more than 20% from a control, or standard.

As used herein, "mildly abnormal" refers to a subject with enough physical characteristics of a disease state to warrant monitoring, but which is not yet to the point of needing treatment. Mildly abnormal can mean about 20-40% or more difference compared to a control. Monitoring can mean that the patient is sent to a specialist for weekly, bi-weekly, monthly, bi-monthly, or yearly monitoring to see if the disease is progressing and needs further treatment.

As used herein, "severely abnormal" refers to a subject with enough physical characteristics of a disease state to warrant treatment for the disease. Severely abnormal can mean 40% or more difference compared to a control or standard. Methods of treatment are discussed below.

Example Methods

Vision loss, commonly caused by one or more ocular diseases, is one of the top causes for disability in adults over the age of 18, and one of the most common disabling conditions in children under the age of 18. Although some ocular diseases have no cure, most are treatable. However, early detection and diagnosis is key for treating, correcting, or slowing most ocular conditions. One of the most common ocular diseases is diabetic retinopathy (DR), which often leads to vision loss. Microaneurysms, tiny protrusions of blood that extend out from an artery or vein of the eye, are usually the first visible sign of DR. However, microaneurysms do not affect vision and often go unnoticed as a result. Acellular capillaries, devoid of epithelial cells and pericytes, appear adjacent to the clusters of microaneurysms. Regions of acellular capillaries in histologic sections correspond to areas of capillary non-perfusion visualized by ancillary ocular imaging. Thus, imaging modalities capable of visualizing changes in retinal microvascular morphology, such as capillary dropout or non-perfusion, are mostly desired for detecting early DR pathology. Optical coherence tomography angiography (OCTA) has emerged as a non-invasive, three-dimensional technique for visualizing the microvasculature of the retina in different layers at micron-scale resolution. It is worth noting that the present invention is not limited to OCTA but can also be applied to other imaging modalities such as fluorescein angiography, indocyanine green angiography, and color fundus photography.

The core principle of OCTA is the detection of Optical coherence tomography (OCT) signal changes over time, caused by the intravascular motion of blood cells. OCTA imaging in this disclosure was performed with Spectralis OCTA Module (manufactured by the Heidelberg Engineering company) using a full-spectrum probabilistic approach. The present invention is not limited to Spectralis OCTA Module but can also be applied to OCTA systems from other manufacturers. Quantitative analyses of retinal capillary dropout using OCTA imaging provides biomarkers of early-stage DR. Vessel density or non-perfusion areas (a compliment of vessel density) has been used as quantitative indices to characterize DR-associated changes in retinal microvasculature, revealing that the total non-perfused area is significantly higher in DR subjects compared to normal controls, and that decreasing vessel density associates with worsening DR. The importance of quantitative assessment of retinal microvasculature in the context of early detection of DR lies in its distinguishing power for mild NPDR. More quantitative imaging tools using OCTA contributes to more accurate detection of early-stage DR. This disclosure present the development and application of a quantitative approach to capture local variations in the retinal microvascular orientation as a biomarker-level predictor of DR using advanced OCTA image analysis.

The orientation of tube-like structures has been of great interest in materials science. For instance, the orientation of individual fibers of steel-fiber reinforced cementitious composites plays an important role in the mechanical properties of the material. Hessian matrix-based analysis offers a useful tool for quantification of tube-like structure on digital images. The matrix of the second-order partial derivative of local structure in an image is termed as the Hessian matrix. In computer vision, early approaches to ridge and valley identification were proposed by Haralick in 1983 utilizing the second directional derivative. Specifically, the eigenvector corresponding to the smallest eigenvalue in absolute value was used to estimate the longitudinal direction of the vessel. Geometrical structure measures calculated from eigenvalues examined the likelihood of the vessel presence in the context of developing a vessel enhancement filter. This vessel filter has been widely used in angiography to improve visualization of human vasculature and served as a preprocessing procedure for the segmentation of blood vessels.

Although the detection of vessel orientation is the intermediate step in the vessel enhancement process, a comprehensive framework for quantification of vessel orientation has never been established in retinal vasculature images. There is a need for a combination of the second derivative and Gaussian multiscale convolution to tune the vesselness filter response that incorporates the eigenvalues, with the objective of enhancing the vessel structure and identifying the retinal vessel width and orientation using, for example, OCTA images. Further, there is a need for the extraction of quantitative metrics from the pattern of retinal vascular orientation, namely, vessel preferred orientation, vessel anisotropy and vessel area, to characterize DR-associated changes in retinal microvasculature. The present disclosure provides methods for quantifying the vascular pattern using ocular imaging that shows vessel profiles.

In one aspect, disclosed herein is a method for treating an ocular vascular disease in a patient in need thereof, the method comprising extracting a retinal vascular feature from an imaging modality obtained from the patient, carrying out a multi-dimensional quantification comprising layer- and sector-based regions of interest (ROIs) to generate a collection of vascular orientation pattern curves, analyzing the vascular orientation pattern curves, placing the patient into a group based on the vascular orientation pattern curve of the patient, wherein said groups comprise (i) a normal range, (ii) a mildly abnormal range, and (iii) a severely abnormal range, and selecting the patient from group ii for further monitoring, and selecting the patient from group iii for treatment.

The ranges discussed above are in relation to a standard, or control. The "control" is defined as a predefined set of criteria by the user which is considered to be a "normal" or "non-diseased" state, or a state which doesn't show predilection to the disease or disorder. A "normal" range is one that does not deviate from the control, or standard, by more than 1%, 2%, 3%, 4%, 5%, 6%, 7%, 8%, 9%, 10%, 11%, 12%, 13%, 14%, 15%, 16%, 17%, 18%, 19%, or 20% or more, less, or in between these values, as determined by one of skill in the art. A "monitored" range is one which deviates from the control, or standard, by 20%, 21%, 22%, 23%, 24%, 25%, 26%, 27%, 28%, 29%, 30%, 31%, 32%, 33%, 34%, 35%, 36%, 37%, 38%, 39%, or 40% or more, less, or in between these values, as determined by one of skill in the art. A "treatment" range is one that deviates from a standard, or control, by 40% or more or less, as determined by one of skill in the art.

It should be noted that the ranges determined above are dependent on the vessel probability (amount of pixels belonging to the vessel) aligned at angles between 0°-180°. Therefore, in one specific example, the vessel of a DR patient aligned between 0°-39° is about 40%-80% different compared to a normal patient in the SVC or the DVC of the IN sector. In another embodiment, the vessel of the DR patient aligned between 40°-79° is about 25%-40% different compared to a normal patient in the SVC or the DVC of the IN sector. In another embodiment, the vessel of the DR patient aligned between 80°-119° is about 0%-20% different compared to a normal patient in the SVC or the DVC of the IN sector. In another embodiment, the vessel of the DR patient aligned between 120°-149° is about 15%-50% different compared to a normal patient in the SVC or the DVC of the IN sector. In another embodiment, the vessel of the DR patient aligned between 150°-180° is about 40%-80% different compared to a normal patient in the SVC or the DVC of the IN sector. In another embodiment, an area under the curve indicates the VAD.

When it is indicated that a patient should be monitored, monitoring can include the patient returning for follow-up medical/clinical care from a physician or a healthcare provider on a schedule or routine interval. In some embodiments, the interval can be on a weekly, monthly, bimonthly (every 2 weeks), biannually (every 6 months), annually, biennially (once every two years) basis. Monitoring can also include the physician or healthcare provider performing basic or routine practices, including, but not limited to measuring blood pressure, weight, height, glucose levels, heart rate, vision examinations, or any other parameters that can affect the patient's vision.

In a specific embodiment, the retinal vascular feature comprises one or more features comprising a vessel distribution intensity (or vessel probability) at a certain angle ranging from 0° to 180°, a retinal sector, and/or a retinal layer. In another embodiment, the retinal vascular feature comprises one or more features comprising a vessel probability (amount of pixels belonging to the vessel) aligned at 1°, 2°, 3°, 4°, 5°, 6°, 7, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, 36°, 37°, 38°, 39°, 40°, 41°, 42°, 43°, 44°, 45°, 46°, 47°, 48°, 49°, 50°, 51°, 52°, 53°, 54°, 55°, 56°, 57°, 58°, 59°, 60°, 61°, 62°, 63°, 64°, 65°, 66°, 67°, 68°, 69°, 70°, 71°, 72°, 73°, 74°, 75°, 76°, 77°, 78°, 79°, 80°, 81°, 82°, 83°, 84°, 85°, 86°, 87°, 88°, 89°, 90°, 91°, 92°, 93°, 94°, 95°, 96°, 97°, 98°, 99°, 100°, 101°, 102°, 103°, 104°, 105°, 106°, 107°, 108°, 109°, 110°, 111°, 112°, 113°, 114°, 115°, 116°, 117°, 118°, 119°, 120°, 121°, 122°, 123°, 124°, 125°, 126°, 127°, 128°, 129°, 130°, 131°, 132°, 133°, 134°, 135°, 136°, 137°, 138°, 139°, 140°, 141°, 142°, 143°, 144°, 145°, 146°, 147°, 148°, 149°, 150°, 151°, 152°, 153°, 154°, 155°, 156°, 157°, 158°, 159°, 160°, 161°, 162°, 163°, 164°, 165°, 166°, 167°, 168°, 169°, 170°, 171°, 172°, 173°, 174°, 175°, 176°, 177°, 178°, 179°, or 180°. In some embodiments, the one or more features comprises a vessel probability (amount of pixels belonging to the vessel) defined across over multiple degrees, e.g., range of 2°, range of 3°, range of 4°. In another embodiment, the retinal sector comprises 1, 2, 3, 4, 5, 6, 7, 8, 9, 10, 11, 12, 13, 14, 15, or 16 equal or unequal sections centered about a macula. In a specific embodiment, the retinal sector comprises 8 equal sections of a macula. When referencing the relative positions of the retinal sectors, the terms "temporal", "nasal", "inferior", or "superior" should be noted and can be used individually or in combination. "Temporal" refers to the anatomical/facial position being closer to the ears, or outer part of the face. "Nasal" refers to the anatomical/facial position being closer to the nose or center of the face. A "superior" position refers to an anatomical position that is towards the head or above a relative starting position. For example, the eyes are superior to the mouth. An "inferior" position refers to an anatomical position that is away from the head or lower relative to a set starting position. For example, the feet are the most inferior part of the body. In another embodiment, the retinal sector comprises at least a temporal-inferior (TI) sector, an inferior-temporal (IT) sector, an inferior-nasal (IN) sector, a nasal-inferior (NI) sector, a nasal-superior (SN) sector, a superior-nasal (SN) sector, a superior-temporal (ST) sector, and a temporal-superior (TS) sector. In another embodiment, the retinal layer is selected from the group comprising a full-projection layer, a superficial vascular plexus (SVP), an intermediate capillary plexus (ICP), a deep capillary plexus (DCP), a superficial vascular complex (SVC), and a deep vascular complex (DVC). In some embodiments, the retinal layer is defined with a specific depth and thickness.

The imaging modality can comprise, but is not limited to, optical coherence tomography angiography (OCTA) modality, fluorescein angiography (FA), indocyanine green angiography (ICGA), or color fundus photography. In another embodiment, the multi-dimensional quantification further comprises a preferred vessel orientation, a vessel anisotropy, and a vessel area density (VAD). In another embodiment, the vascular orientation pattern captures local variations in the vessel orientation.

In some embodiments, the ocular vascular disease is an ocular disease of the retina, sclera, choroid, or any related tissue involving abnormal or excessive blood or lymph vessels. In some embodiments, the ocular vascular disease, including, but are not limited to diabetic retinopathy (DR), proliferative diabetic retinopathy (PDR), nonproliferative diabetic retinopathy (NPDR), neovascular and dry age-related macular degeneration, geographic atrophy, central serous retinopathy, cystoid macular edema, diabetic macular edema, rubeosis iridis, retinopathy of prematurity, central or branch retinal vein occlusions, inflammatory/infectious retinal neovascularization/edema (i.e.: posterior uveitis, sarcoid, toxoplasmosis, histoplasmosis, Vogt-Koyanagi-Harada Disease, multifocal choroiditis, chronic uveitis, tuberculosis, syphilis, punctate and multifocal inner choroidopathy), retinoblastoma, ocular tumors, retinal detachment, myopic neovascularization, angioid streaks, Eales Disease, Coats Diseases, Sorsby's fundus dystrophy, ischemic retinopathy (retinal artery occlusion, Takayasu's Disease, carotid artery occlusion), and choroidal rupture is treated or prevented by the methods of the disclosure.

In one embodiment, the retinal vascular disease is selected from any one of the groups consisting of diabetic retinopathy, macular degeneration, retinal vein occlusions, retinopathy of prematurity, retinal artery microaneurysm, hypertension (including hypertensive retinopathy and other hypertension-related diseases such as preeclampsia), atherosclerosis, vasculitis, blood dyscrasia, a systemic infection, radiation exposure, lupus, AIDs, or any other disease associated with retinopathy. In another embodiment, the patient is being monitored for any retinal vascular disease of any preceding embodiment. In another embodiment, the patient in the treatment range receives a treatment corresponding to the retinal vascular disease. In another embodiment, the treatment is anti-vascular endothelial growth factors (anti-VEGF), laser, and/or gene therapy. In some embodiments, the patient is a vertebrate or non-vertebrate. In other embodiments, the patient is a mammal. In other embodiments, the patient is a reptile, amphibian, or fish. In other embodiments, the patient is a non-human primate. In other embodiments, the patient is a human.

When a patient is selected to the treatment group, the treatment can include, but is not limited to retinal laser therapy (laser photocoagulation), intraocular or intravitreal injections of an anti-VEGF medications or steroid medications, a vitrectomy surgical procedure, or medications to control blood glucose levels (i.e.: insulins, Pramlintide, Precose, Glyset, biguanides, Bromocriptine, Dipeptidyl peptidase inhibitors-4 (DPP-4), glucagon-like peptide-1 receptor agonists (GLP-1 receptor agonist), Meglitinides, sodium-glucose transporter (SGLT) 2 inhibitors, sulfonylureas, thiazolidinediones, or acetaminophen), blood pressure levels (i.e.: thiazide diuretics, potassium-sparing diuretics, loop diuretics, combination diuretics, beta-blockers, angiotensin converting enzyme (ACE) inhibitors, Angiotensin II receptor blockers (ARBs), calcium channel blockers, alpha-blockers, alpha-beta blockers, central agonists, vasodilators, aldosterone receptor antagonists, or direct renin inhibitors), or cholesterol levels (i.e.: statins, cholesterol absorption inhibitors, bile acid sequestrants, PCSK9 inhibitors, adenosine triphosphate-citrate lyase (ACL) inhibitors, fibrates, niacin, or omega-3 fatty acid ethyl esters). In some embodiments, the treatment can also include gene therapy, wherein suitable carriers deliver genetic material such as DNA or RNA, to the site of interest, including, but not limited to use of viral vectors (i.e.: associated adenoviral vectors (AAV), adenoviral vectors (Ad), equine infectious anaemia virus (EIAV), human immunodeficiency virus (HIV), simian immunodeficiency virus (SIV), lentiviruses, and other viral variants), DNA nanoparticles, or electroporation and lipofection.

In another aspect, a method is disclosed for screening an ocular vascular disease progression in a patient, wherein the disease progression is indicated by a change in a vessel orientation distribution.

In some embodiments, the method of screening can be performed during any routine medicial/clinical visit with a healthcare provider. In some embodiments, method of screening is performed during an annual eye exam.

In some embodiments, the change in the vessel orientation distribution is a 10% or more increase compared to a normal patient in a SVC or a DVC. In some embodiments, the change in the vessel orientation distribution is a 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% increase compared to a normal patient in the SVC or the DVC.

In some embodiments, the disease progression is screened about every 365 days. In some embodiments, the disease progression is screened about every 14 days, 30 days, 60 days, 90 days, 180 days, 270 days, or 365 days. In some embodiments, the disease progression is screened about every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, or 365 days.

In some embodiments, the ocular vascular disease is a retinal vascular disease.

In some embodiments, the ocular vascular disease is an ocular disease of the sclera, choroid, or any related tissue involving abnormal or excessive blood or lymph vessels. In some embodiments, the ocular vascular disease, including, but are not limited to diabetic retinopathy (DR), proliferative diabetic retinopathy (PDR), nonproliferative diabetic retinopathy (NPDR), neovascular and dry age-related macular degeneration, geographic atrophy, central serous retinopathy, cystoid macular edema, diabetic macular edema, rubeosis iridis, retinopathy of prematurity, central or branch retinal vein occlusions, inflammatory/infectious retinal neovascularization/edema (i.e.: posterior uveitis, sarcoid, toxoplasmosis, histoplasmosis, Vogt-Koyanagi-Harada Disease, multifocal choroiditis, chronic uveitis, tuberculosis, syphilis, punctate and multifocal inner choroidopathy), retinoblastoma, ocular tumors, retinal detachment, myopic neovascularization, angioid streaks, Eales Disease, Coats Diseases, Sorsby's fundus dystrophy, ischemic retinopathy (retinal artery occlusion, Takayasu's Disease, carotid artery occlusion), and choroidal rupture is treated or prevented by the methods of the disclosure.

In one embodiment, the retinal vascular disease is selected from any one of the groups consisting of diabetic retinopathy, macular degeneration, retinal vein occlusions, retinopathy of prematurity, retinal artery microaneurysm, hypertension (including hypertensive retinopathy and other hypertension-related diseases such as preeclampsia), atherosclerosis, vasculitis, blood dyscrasia, a systemic infection, radiation exposure, lupus, AIDs, or any other disease associated with retinopathy.

Example Software

Figure 12A:
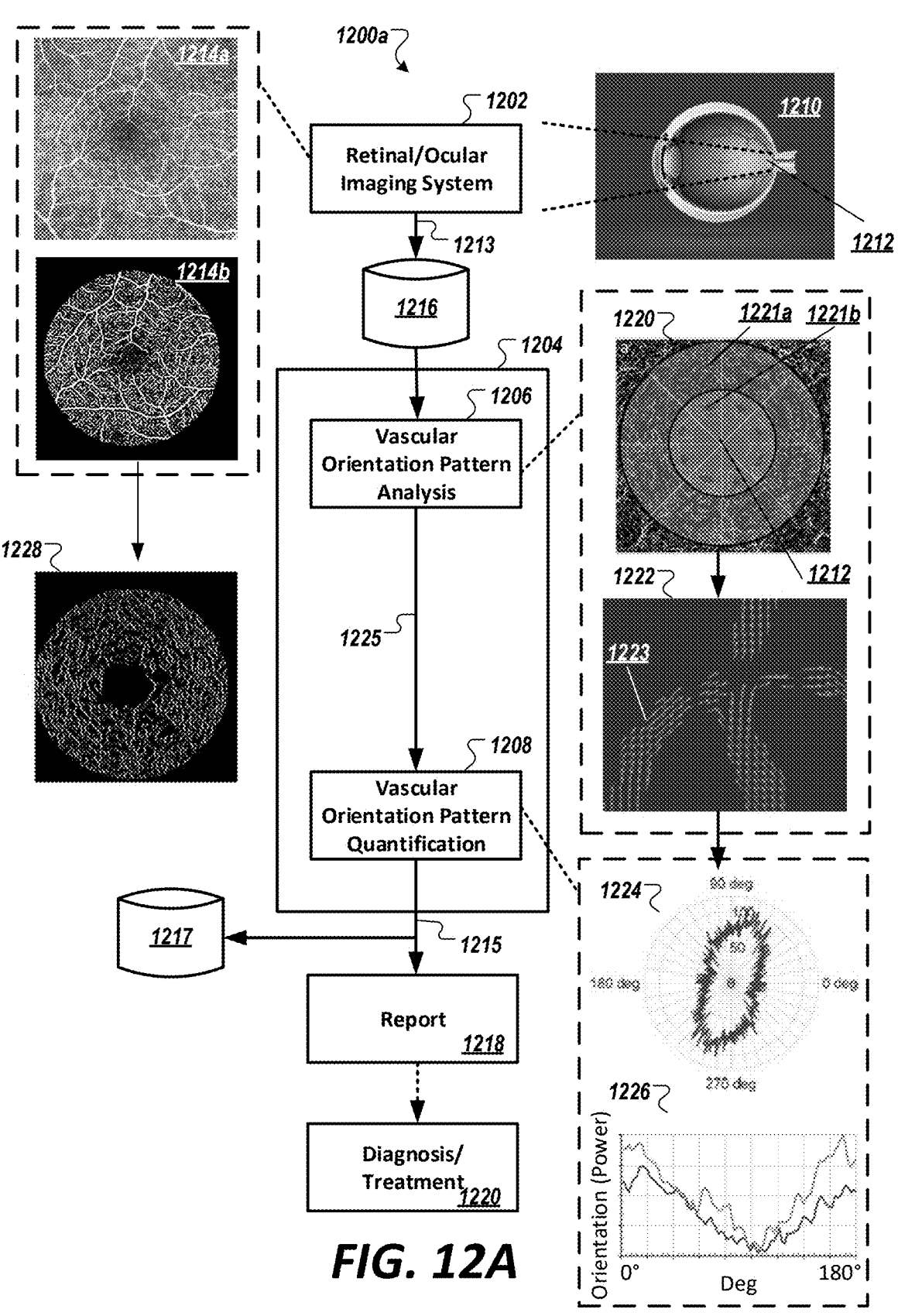
FIGS. 12A and 12B show example systems to perform ocular or retinal vascular disease assessment based on vasculature orientations of an acquired ocular or retinal vascular image.
Figure 12B:
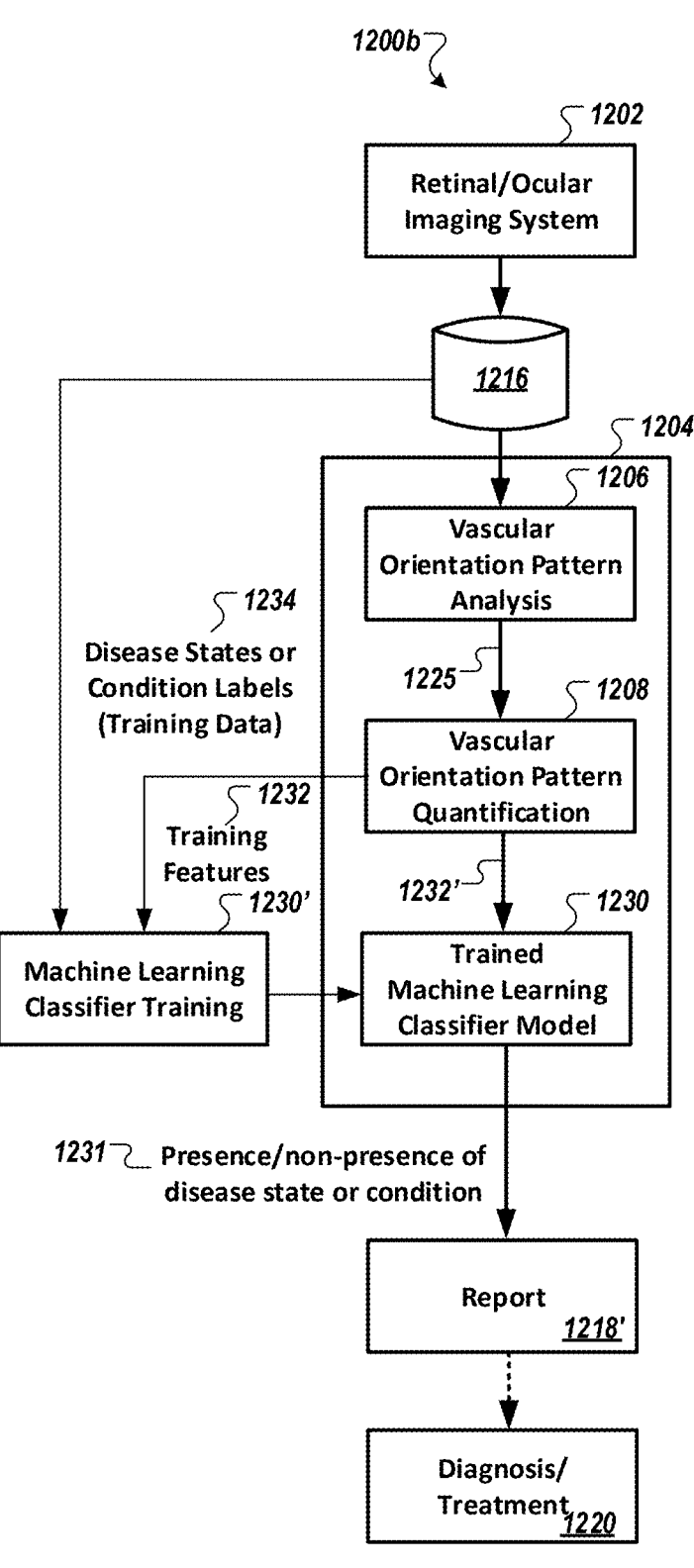

Example System #1. FIGS. 12A and 12B show example systems 1200 (shown as 1200a, 1200b) to perform ocular or retinal vascular disease assessment based on vasculature orientations of an acquired ocular or retinal vascular image. In the example shown in FIG. 12A, the system 1200a includes a retinal/ocular imaging system 1202 and an analysis system 1204 having a vascular orientation pattern analysis module 1206 and a vascular orientation pattern quantification module 1208.

The retinal/ocular imaging system 1202 is configured to acquire optical coherence tomography angiography (OCTA), fluorescein angiography (FA), indocyanine green angiography (ICGA), or color fundus photography from at least one eye 1210 of a patient, including of the retina vasculature, e.g., around the macula 1212. The ocular or retinal vascular data may include 2D ocular or retinal vascular data, 3D ocular or retinal vascular data, time-dependent ocular or retinal vascular data, or data of the imaging modality data described herein. The acquired data 1213 are provided to a data store 1216, which can be (i) a local data store or (ii) a remote data store, e.g., located in cloud infrastructure, e.g., provided over a network. FIG. 12A shows an OCTA image (shown as 1214a) as an example of an ocular or retinal vascular image or file 1213.

The analysis system 1204 is configured to retrieve an ocular or retinal vascular image or file 1213 from the data store 1216 to perform the analysis to generate an assessment output 1215 for a report 1218. The report 1218 can be used by a physician, clinician, researcher in the diagnosis, or treatment, (shown as 1218) of an ocular or retinal disease or condition, e.g., diabetic retinopathy, macular degeneration, retinal vein occlusions, retinopathy of prematurity, retinal artery microaneurysm, hypertension (including hypertensive retinopathy and other hypertension-related diseases such as preeclampsia), atherosclerosis, vasculitis, blood dyscrasia, a systemic infection, radiation exposure, lupus, AIDs, or any other disease associated with retinopathy, among others described herein. In some embodiments, the assessment output 1215 is provided to a second data store 1217 (or data store 1216). The report 1218 may be curated to the physician, clinician, researcher and/or the patient through a healthcare portal. In some embodiments, the assessment output 1215 and/or report 1217 are provided to a health provider (not shown) to provide the assessment output 1215 and/or report 1217 to the physician, clinician, researcher, and/or the patient.

The vascular orientation pattern analysis module 1206 includes computer-readable instructions to determine a set of orientation vectors (shown in diagram 1222) at each pixel (1223), or a set of pixels, of a set of pre-defined regions (shown in diagram 1220) of the ocular or retinal vascular image or object 1214a. Image 1214b shows an example region of interest segmented from the ocular or retinal vascular image or object 1214a to which the analysis can be performed.

As shown in diagram 1220, the vascular orientation pattern analysis module 1206 may identify a set of pre-defined regions (e.g., 1221a, 1221b) in pre-defined segments/regions, e.g., centered around the macula 1223. In the example shown in FIG. 12A, at least 8 regions 1221a (or 1221b) are analyzed, e.g., for the regions of the nasal superior (NS), superior nasal (SN), nasal inferior (NI), inferior nasal (IN), temporal inferior (TI), inferior temporal (TI), temporal superior (TS), superior temporal (ST). In some embodiments, the vascular orientation pattern analysis module 1206 is configured to determine the orientation vectors (e.g., per diagram 1222) by generating a Hessian matrix of intensity values of the ocular or retinal vascular image or object and determining eigenvector corresponding to the smallest eigenvalue in magnitude of the Hessian matrix, e.g., as later described in relation to Equations 1-6. Other methods of determining the orientation vectors may be employed.

The vascular orientation pattern quantification module 1208 is operatively connected to the vascular orientation pattern analysis module 1206 to quantify the vascular orientation patterns 1225. In some embodiments, the vascular orientation pattern quantification module 1208 is configured to aggregate all the vasculature vectors, or the number of vectors, of the vascular orientation patterns 1225 for a given orientation values between 0° and 180°, e.g., in 10 increment or other degree of increments as described herein. Diagram 1224 shows a plot of the aggregation, also referred to as a quantification or quantification metric, for one of the segments/regions 1221a. The output 1215 can be mapped to the region of interest 1214b to generate a color map 1228 of the segments/regions 1221a.

In some embodiments, the analysis system 1204 is integrated with the retinal/ocular imaging system 1202. In other embodiments, the analysis system 1204 is a separate infrastructure that operates with the retinal/ocular imaging system 1202. In some embodiments, the system 1200 is configured as a hand-held device.

Example Method of Operation. FIG. 13 shows an example method 1300 of operation of the system of FIG. 12. Method 1300 includes receiving 1302 a data set comprising ocular or retinal vascular image or object. The ocular or retinal vascular data may include 2D ocular or retinal vascular data, 3D ocular or retinal vascular data, time-dependent ocular or retinal vascular data, or data of the imaging modality data described herein.

Method 1300 includes the step of determining 1304, e.g., using a second derivative edge detection operation, a set of orientation vectors at each pixel of a set of pre-defined regions of the ocular or retinal vascular image or object, including a first region and a second region. The orientation vectors may be determined by generating a Hessian matrix of intensity values of the ocular or retinal vascular image or object and determining eigenvector corresponding to the smallest eigenvalue in magnitude of the Hessian matrix, e.g., as described herein in relation to Equations 1-6.

Method 1300 includes the step of determining 1306 a set of first quantification metrics from the set of orientation vectors for at least the first region and a set of second quantification metrics from the set of orientation vectors for the second region. The first and second sets of quantification metrics, among others, may then be employed in a diagnosis or a treatment of an ocular or retinal vascular disease. The set of orientation vectors represents the vascular orientation pattern capturing local variations in the vessel orientation, e.g., ranging from 0 to 180° or other ranges described herein.

The quantification metrics may be generated for a set of 8 pre-defined retinal sectors centered at an identified landmark corresponding to the macula or for any number of retinal sectors as described herein. Examples of the quantification metrics include aggregation or sum of a number of orientation vectors in a pre-defined angle or angular range, e.g., as described in relation to FIGS. 5B-5I.

The vascular orientation pattern could be quantified and/or displayed in two types of plots (polar 1224 & Cartesian 1226). For the polar plot, the pattern depicts a roughly elliptical shape with a major axis and a minor axis (FIG. 4), and by analyzing the shape, three independent quantitative metrics were defined to facilitate direct numerical comparison among different eyes/cohorts. These three metrics are preferred orientation, vessel anisotropy, and vessel area and are obtained by using the Matlab function "regionprops". The preferred orientation is identified by the angle between the x-axis and the major axis of the ellipse that has the same second moments as the region. The value is in degree, ranging from 0 to 180 degrees. The ratio of major axis length and minor axis length is defined as vessel anisotropy. The Major(minor) axis length is the length in pixel of the major (minor) axis of the ellipse that has the same normalized second central moments as the region. The vessel area is defined as the number of pixels in the region.

For the Cartesian plot, the vascular orientation pattern curve provides an explicit way to show the distribution of the vessels that can be easily understood by clinicians and patients. In addition, the Cartesian plot can be used to track the disease progression at different time points, and to illustrate where the local vessel probability deviates from a normative database (FIG. 10).

Regardless of the type of display (1224 or 1226), 180 metrics/features (or interpolated version thereof) may be employed or shown that constitute the orientation pattern for a specific region of interest (ROI), and they are the vessel probability at each angle from 0 to 180 degrees. Those 180 features could be readily used as input for machine learning models with interpretability for the results.

Method 1300 further includes outputting (1310) the quantification metrics or indication of the presence or non-presence of a disease state determined from such quantification metrics (e.g., in a report for use in diagnostics or as signals for controls).

Example System #2. FIG. 12B shows another example system 1200b to perform ocular or retinal vascular disease assessment using machine learning/AI operations of the vasculature orientations of an acquired ocular or retinal vascular image. The analysis system 1204 (shown as 1204') is shown with a trained machine learning classifier mode 1230 that can generate an indication 1231 for a presence or non-presence of a disease state or condition (e.g., an ocular or retinal disease or condition). The trained machine learning classifier mode 1230 is configured to employ a subset of the quantification metrics 1232 generated during the training phase of the training module 1230' (shown as Machine Learning Classifier Training Module 1230'). In the example shown in FIG. 12B, labeled disease state or condition (1234) may be provided to the training module 1230'. In other embodiments, the images may be evaluated with other features 1232. The features 1232, when used in the training, can reduce the number of training data set required to generate the trained machine learning classifier model 1230.

Example Machine Learning Neural Network Assessment. In some embodiments, the first and second sets of quantification metrics may be used by a trained machine learning or neural network to output an indication of a presence or non-presence of ocular or retinal vascular disease, wherein the trained machine learning or neural network was trained using orientation vectors at each pixel of pre-defined regions of a training data set comprising ocular or retinal vascular images or objects and labels for the ocular or retinal vascular disease.

Machine Learning. The term "artificial intelligence" (e.g., as used in the context of AI system) can include any technique that enables one or more computing devices or computing systems (i.e., a machine) to mimic human intelligence. Artificial intelligence (AI) includes but is not limited to knowledge bases, machine learning, representation learning, and deep learning. The term "machine learning" is defined herein to be a subset of AI that enables a machine to acquire knowledge by extracting patterns from raw data. Machine learning techniques include, but are not limited to, logistic regression, support vector machines (SVMs), decision trees, Naïve Bayes classifiers, and artificial neural networks. The term "representation learning" is defined herein to be a subset of machine learning that enables a machine to automatically discover representations needed for feature detection, prediction, or classification from raw data. Representation learning techniques include, but are not limited to, autoencoders. The term "deep learning" is defined herein to be a subset of machine learning that enables a machine to automatically discover representations needed for feature detection, prediction, classification, etc., using layers of processing. Deep learning techniques include but are not limited to artificial neural networks or multilayer perceptron (MLP).

Machine learning models include supervised, semi-supervised, and unsupervised learning models. In a supervised learning model, the model learns a function that maps an input (also known as feature or features) to an output (also known as target or target) during training with a labeled data set (or dataset). In an unsupervised learning model, the model has a pattern in the data. In a semi-supervised model, the model learns a function that maps an input (also known as feature or features) to an output (also known as a target) during training with both labeled and unlabeled data.

Neural Networks. An artificial neural network (ANN) is a computing system including a plurality of interconnected neurons (e.g., also referred to as "nodes"). This disclosure contemplates that the nodes can be implemented using a computing device (e.g., a processing unit and memory as described herein). The nodes can be arranged in a plurality of layers such as an input layer, an output layer, and optionally one or more hidden layers. An ANN having hidden layers can be referred to as a deep neural network or multilayer perceptron (MLP). Each node is connected to one or more other nodes in the ANN. For example, each layer is made of a plurality of nodes, where each node is connected to all nodes in the previous layer. The nodes in a given layer are not interconnected with one another, i.e., the nodes in a given layer function independently of one another. As used herein, nodes in the input layer receive data from outside of the ANN, nodes in the hidden layer(s) modify the data between the input and output layers, and nodes in the output layer provide the results. Each node is configured to receive an input, implement an activation function (e.g., binary step, linear, sigmoid, tan H, or rectified linear unit (ReLU) function), and provide an output in accordance with the activation function. Additionally, each node is associated with a respective weight. ANNs are trained with a dataset to maximize or minimize an objective function. In some implementations, the objective function is a cost function, which is a measure of the ANN's performance (e.g., error such as L1 or L2 loss) during training, and the training algorithm tunes the node weights and/or bias to minimize the cost function. This disclosure contemplates that any algorithm that finds the maximum or minimum of the objective function can be used for training the ANN. Training algorithms for ANNs include but are not limited to backpropagation. It should be understood that an artificial neural network is provided only as an example machine learning model. This disclosure contemplates that the machine learning model can be any supervised learning model, semi-supervised learning model, or unsupervised learning model. Optionally, the machine learning model is a deep learning model. Machine learning models are known in the art and are therefore not described in further detail herein.

A convolutional neural network (CNN) is a type of deep neural network that has been applied, for example, to image analysis applications. Unlike traditional neural networks, each layer in a CNN has a plurality of nodes arranged in three dimensions (width, height, depth). CNNs can include different types of layers, e.g., convolutional, pooling, and fully-connected (also referred to herein as "dense") layers. A convolutional layer includes a set of filters and performs the bulk of the computations. A pooling layer is optionally inserted between convolutional layers to reduce the computational power and/or control overfitting (e.g., by downsampling). A fully-connected layer includes neurons, where each neuron is connected to all of the neurons in the previous layer. The layers are stacked similarly to traditional neural networks. GCNNs are CNNs that have been adapted to work on structured datasets such as graphs.

Other Supervised Learning Models. A logistic regression (LR) classifier is a supervised classification model that uses the logistic function to predict the probability of a target, which can be used for classification. LR classifiers are trained with a data set (also referred to herein as a "dataset") to maximize or minimize an objective function, for example, a measure of the LR classifier's performance (e.g., an error such as L1 or L2 loss), during training. This disclosure contemplates that any algorithm that finds the minimum of cost function can be used. LR classifiers are known in the art and are therefore not described in further detail herein.

A Naïve Bayes' (NB) classifier is a supervised classification model that is based on Bayes' Theorem, which assumes independence among features (i.e., the presence of one feature in a class is unrelated to the presence of any other features). NB classifiers are trained with a data set by computing the conditional probability distribution of each feature given a label and applying Bayes' Theorem to compute the conditional probability distribution of a label given an observation. NB classifiers are known in the art and are therefore not described in further detail herein.

A k-NN classifier is a supervised classification model that classifies new data points based on similarity measures (e.g., distance functions). The k-NN classifiers are trained with a data set (also referred to herein as a "dataset") to maximize or minimize a measure of the k-NN classifier's performance during training. The k-NN classifiers are known in the art and are therefore not described in further detail herein.

A majority voting ensemble is a meta-classifier that combines a plurality of machine learning classifiers for classification via majority voting. In other words, the majority voting ensemble's final prediction (e.g., class label) is the one predicted most frequently by the member classification models. The majority voting ensembles are known in the art and are therefore not described in further detail herein.

Example Computing Environment. An exemplary computing environment that may implement the retinal microvasculature analysis described herein may include various numerous computing devices environments or configurations. Examples of computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments (e.g., implemented in cloud infrastructure) that include any of the above systems or devices, and the like.

Computer-executable instructions, such as program modules, being executed by a computer may be used. Generally, program modules include routines, programs, objects, components, data structures, etc., that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media, including memory storage devices.

An exemplary system, in its most basic configuration, may include at least one processing unit and memory. A processing unit may include one or more processing elements (e.g., reduced instruction set computing (RISC) cores or complex instruction set computing (CISC) cores, etc.) that can execute computer-readable instructions to perform a pre-defined task or function. Depending on the exact configuration and type of computing device, memory may be volatile (such as random-access memory (RAM)), non-volatile (such as read-only memory (ROM), flash memory, etc.), or some combination of the two.

The computing device may have additional features/functionality. For example, the computing device may include additional storage (removable and/or non-removable), including, but not limited to, magnetic or optical disks or tape.

The computing device may include a variety of computer-readable media. Computer-readable media can be any available media that can be accessed by the device and includes both volatile and non-volatile media, removable and non-removable media.

Computer storage media include volatile and non-volatile, and removable and non-removable media implemented in any method or technology for storage of information such as computer-readable instructions, data structures, program modules, or other data. Memory, removable storage, and non-removable storage are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by the computing device. Any such computer storage media may be part of the computing device.

The computing device may contain communication connection(s) that allow the device to communicate with other devices. The computing device may also have input device(s) such as a keyboard, mouse, pen, voice input device, touch input device, etc. Output device(s) such as a display, speakers, printer, etc., may also be included. All these devices are well known in the art and need not be discussed at length here.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

EXAMPLES

The following examples are set forth below to illustrate the compositions, devices, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1: Quantifying the Pattern of Retinal Vascular Orientation in Diabetic Retinopathy Using Optical Coherence Tomography Angiography Quantitative imaging using optical coherence tomography angiography (OCTA) provides objective tools for the detection and characterization of diabetic retinopathy (DR). In this example, an operator combining the second derivative and Gaussian multiscale convolution is applied to identify the retinal orientation at each pixel in the OCTA image. The pattern of retinal vascular orientation was quantified and three novel quantitative metrics including vessel preferred orientation, vessel anisotropy, and vessel area were developed. Each of eight 45° sectors of the circular disk centered at the macular region was defined as the region of interest. Significant sectoral differences were observed in the preferred orientation ($p<0.0001$) and vessel area ($p<0.0001$) in the 34 healthy subjects, whereas vessel anisotropy did not demonstrate a significant difference among the eight sectors ($p=0.054$). Differential retinal microvascular orientation patterns were observed between healthy controls ($n=34$) and the DR subjects ($n=7$). The vessel area characterized from the vascular orientation pattern was shown to be strongly correlated with the traditionally reported vessel density (Pearson $R>0.97$, $p<0.0001$). With three metrics calculated from the vascular orientation pattern simultaneously and sectorally, the quantitative assessment for retinal microvasculature provides more information than vessel density alone and thereby enhances the detection of DR. These results show the feasibility and advantage of vessel orientation-based quantitative approach using OCTA to characterize DR-associated changes in retinal microvasculature.

Example Methods

Second Derivative Edge Detection

Herein, the second derivative of the intensity in a gray-scale image is used as an edge-detection operator. Zero-crossings of the second derivative for a continuous intensity profile correspond to the local maxima in the gradient of the image (first derivative) (FIG. 1A-1D). For a vessel modeled as a tube with a 2-dimensional Gaussian profile with standard deviation $s=1$, as specified by $$I_0 = \frac{1}{2\pi s^2} \exp\left(\frac{-x^2}{2s^2}\right)$$

(FIG. 1B), the Hessian matrix can be expressed in Equation 1 as $$H_0 = \begin{bmatrix} \frac{\partial^2 I_0}{\partial x^2} & \frac{\partial^2 I_0}{\partial x \partial y} \\ \frac{\partial^2 I_0}{\partial x \partial y} & \frac{\partial^2 I_0}{\partial y^2} \end{bmatrix} = \begin{bmatrix} (x^2-1)I_0 & 0 \\ 0 & 0 \end{bmatrix} \qquad \text{(Eq. 1)}$$

Eigenvectors ($v_1$, $v_2$) and eigenvalues ($\lambda_1$, $\lambda_2$; $|\lambda_1|<|\lambda_2|$),) of the Hessian matrix $H_0$ are shown in Equation Set 2.

$$\lambda_1=0;\ v_1=(0,1)$$

$$\lambda_2=(x^2-1)I_0;\ v_2=(1,0) \qquad \text{(Eq. Set 2)}$$

The orientation of the vessel $I_0$ is along the y-direction, as shown in FIG. 1A, and is the same as the eigenvector corresponding to the smallest eigenvalue in magnitude, i.e., $v_1$.

For an angiography image, the intensity takes a general form I (t) shown in Equation 3 which can be approximated by its Taylor expansion in the neighborhood of a point $t_0$ up to the second order to analyze the local structure.

$$I(t) \approx I(t_0) + \Delta t^T \nabla I(t_0) + \frac{1}{2} \Delta t^T H(I(t_0)) \Delta t \qquad \text{(Eq. 3)}$$

In Equation 3, $\Delta t=t-t_0$, $\nabla I(t_0)$ and $H(I(t_0))$ are the gradient vector and Hessian matrix of the image I (t) computed at the point $t_0$. The third term in Equation can provide the second-order directional derivatives shown in Equation 4.

$$\Delta t^T H(I(t_0)) \Delta t = \left(\frac{\partial}{\partial t_0}\right)\left(\frac{\partial}{\partial t_0}\right) I(t_0) \qquad \text{(Eq. 4)}$$

Using Equation 1 and Equation Set 2 with an ideal continuous intensity profile for vessel modeling, eigenvalue and eigenvector analysis of the Hessian matrix can be used to establish the vessel orientation per Equation 5. Eigenvector defining the direction can be scaled up by the linear transformation per Equation 6.

$$H(I(t_0))v=\lambda v \qquad \text{(Eq. 5)}$$

$$v^T H(I(t_0))v=\lambda \qquad \text{(Eq. 6)}$$

The similarity between Equation 4 and Equation 6 in terms of composition illustrates an association of eigenvalue and the second-order structure of the image. Two orthonormal directions are mapped by the Hessian matrix onto the eigenvalues. A circle neighborhood centered at $t_0$ is mapped by the Hessian matrix onto the second-order structure of the image. The eigenvalues extracted from the Hessian matrix describe the strength of the grey-scale variation in all directions for the pixel of interest. The eigenvector, of the smallest eigenvalue (by absolute value) corresponding to the smallest variation in those grey-scale values, delineates the orientation of the vessel in the angiography image at a specific pixel.

Multiscale Convolution

Multi-scale analysis is imperative to detect the vessels with various widths in the angiography image. When incorporating the scale $\sigma$, linear scale space theory is applied to ensure the well-posed properties of the differential operator of I, such as the gradient vector and Hessian matrix. In this framework differentiation is calculated by a convolution with derivatives of Gaussians per Equation 7.

$$\frac{\partial}{\partial t} I(t, \sigma) = I(t) * \frac{\partial}{\partial t} G(t, \sigma) \qquad \text{(Eq. 7)}$$

In Equation 7, the symbol * denotes the convolution, and a Gaussian kernel of width $\sigma$ is given per Equation 8.

$$G(t, \sigma) = \frac{1}{2\pi\sigma^2} \exp\left(\frac{-\|t\|^2}{2\sigma^2}\right) \qquad \text{(Eq. 8)}$$

In Equation 8, $\|t\|^2$ is the squared length of vector t, i.e., $x^2 + y^2$. The partial second derivative of $I(t, \sigma)$ in the Hessian matrix can be replaced by the partial second derivative of Gaussian, for example, as shown in Equation 9.

$$I_{xx}(t, \sigma) = I(t) * \frac{\partial^2}{\partial^2 x} G(t, \sigma) \qquad \text{(Eq. 9)}$$

Convolving the image with a Gaussian function can smooth out the image background noise and enhance image vessel structures. The eigenvectors and eigenvalues of the Hessian matrix depends on the scale $\sigma$ of the Gaussian, and therefore are denoted as, $v_i(t, \sigma)$ and $\lambda_i(t, \sigma)$, respectively ($i=1,2; |\lambda_1| < |\lambda_2|$). The condition of a line can be regarded as $\lambda_1 \approx 0$ (for an ideal line, $\lambda_1 = 0$), thus the ratio of eigenvalues R has been suggested as a similarity measure of a line structure as shown in Equation 10.

$$R = \frac{|\lambda_1(t, \sigma)|}{|\lambda_2(t, \sigma)|} \qquad \text{(Eq. 10)}$$

In addition to geometric measure for vessels, another important measure is defined to distinguish the vessel from the background noise, termed as a structure-ness measure per Equation 11.

$$S = \sqrt{\lambda_1^2(t, \sigma) + \lambda_2^2(t, \sigma)} \qquad \text{(Eq. 11)}$$

The structure-ness measure S is low for the background when there is no presence of the vessel structure as the eigenvalues are small due to the lack of contrast. With these two measures, ratio of eigenvalues R and structure-ness measure S, a filter response function can be defined to detect the vessels with different widths per Equation 12.

$$\rho(t, \sigma) = \exp\left(-\frac{R^2}{2\beta^2}\right)\left(1 - \exp\left(-\frac{S^2}{2\gamma^2}\right)\right) \qquad \text{(Eq. 12)}$$

In Equation 12, the terms $\beta$ and $\gamma$ are suppression index. This filter can be examined at different scales, e.g., in the range of $\sigma_{min} \leq \sigma \leq \sigma_{max}$, which can cover the range of vessel width in the angiography image. The strongest response can indicate the identification of vessel width at a specific pixel per Equation 13.

$$\rho(t) = \max_{\sigma_{min} \leq \sigma \leq \sigma_{max}} \rho(t, \sigma) \qquad \text{(Eq. 13)}$$

The filter response is maximum when the scale matches the width of the vessel, $\sigma_0$. The vessel orientation can be estimated as $v_1(t, \sigma_0)$, i,e, the eigenvector corresponding to the smallest eigenvalue in magnitude $\lambda_1(t, \sigma_0)$. Overall, this vesselness filter allows enhancing the vessel-background segmentation and detecting the vessel width and orientation simultaneously. The enhancement quality and efficiency were regulated by four filter parameters, i.e., scale range $[\sigma_{min} \ \sigma_{max}]$, and suppression index, $\beta$ and $\gamma$. They were empirically determined by approximating the size (in pixels) of the vessel width and evaluating the noise and background suppression.

Figure 2A:
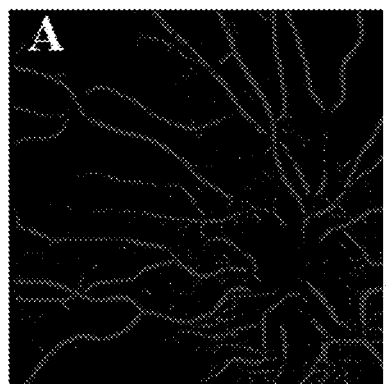
FIGS. 2A-2B show an illustration of vessel orientation extraction from OCTA image.
Figure 2B:
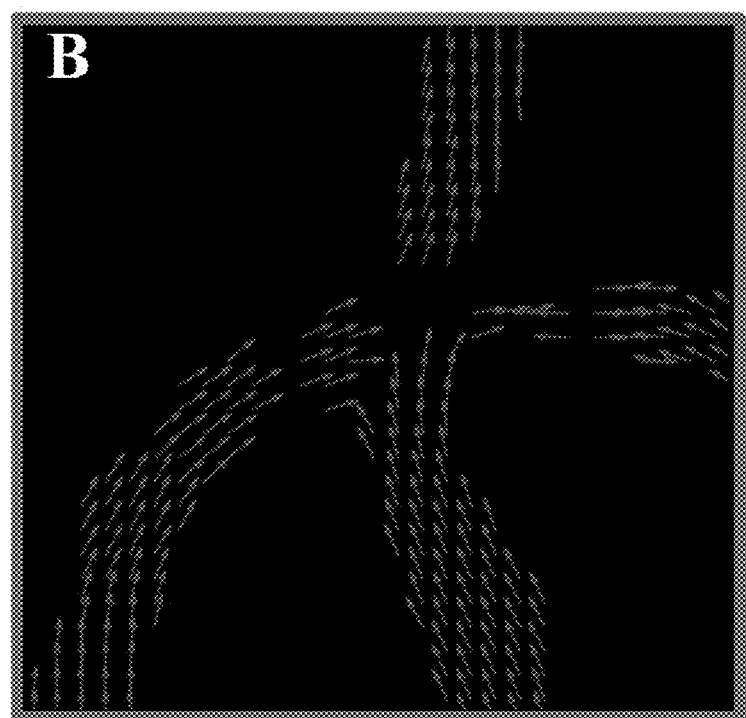
Figure 3A:
FIGS. 3A, 3B, and 3C show the visualization of retinal microvascular orientation.
Figure 3A:
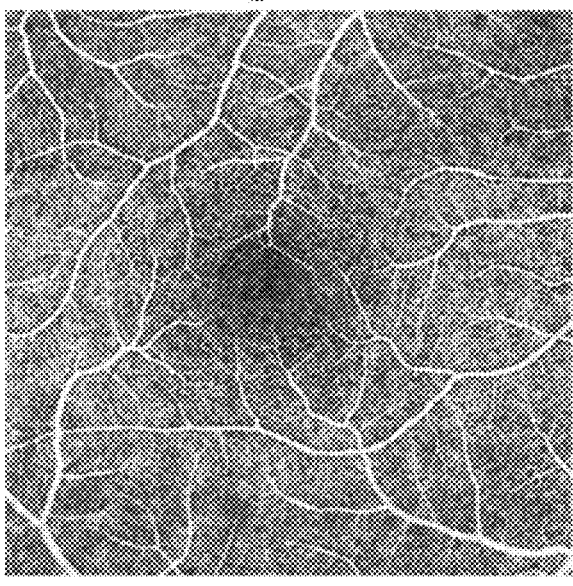
Figure 3B:
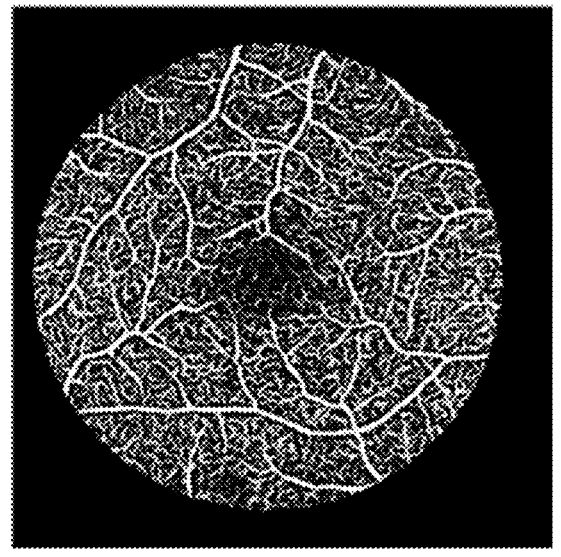
Figure 3C:
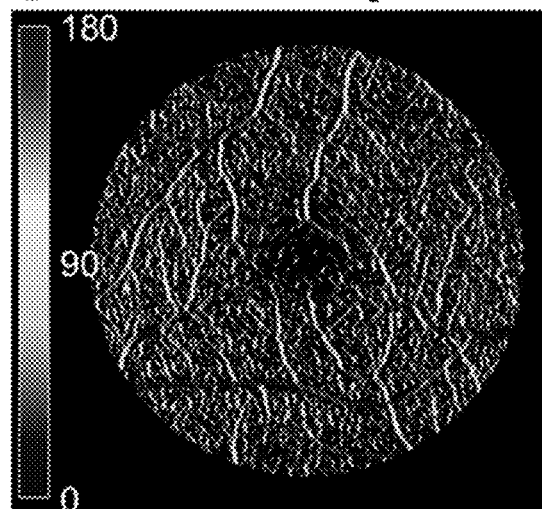

Pattern of Retinal Vascular Orientation: Preferred Orientation, Anisotropy and Vessel Area Localized changes in retinal microvascular orientation have not been quantified from OCTA images. FIG. 2A illustrates the vessel orientation extraction from a representative OCTA image. Note that the orientation of the retinal vessel is identified at each pixel, denoted by the arrows (FIG. 2B). In addition to the vesselness filter, the binary filter was applied prior to the Hessian matrix-based method to extract the vessel orientation in the region of interest (ROI). Binary filter with a fixed threshold was limited by the fact that the noise level varies among scans and even within the same scan due to deviations in the OCT reflectance signal. In contrast, a binary vessel mask was created with a globally determined threshold using Otsu's method, which chooses the threshold value to minimize the intra-class variance of the black and white pixels in the image. Color maps were generated to visualize the local vessel orientation in the ROI (FIGS. 3A-3C).

Figure 4A:
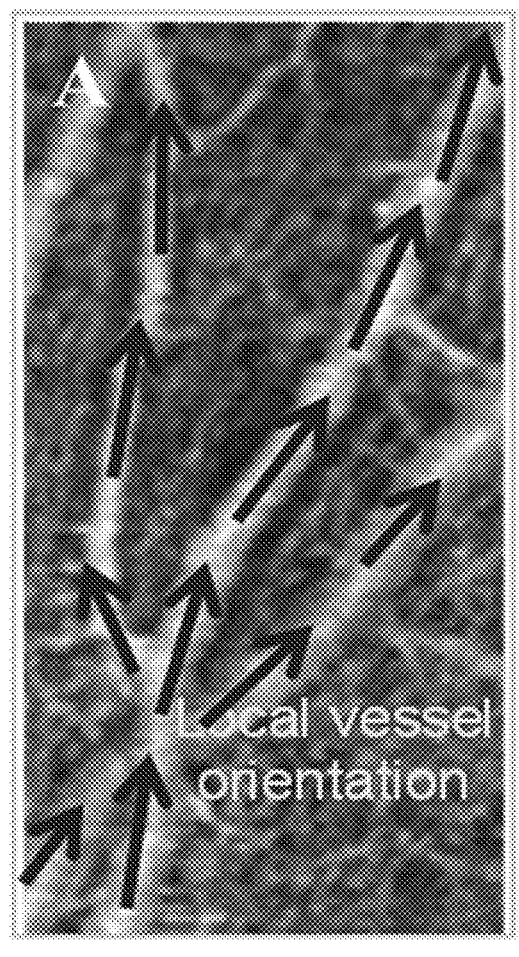
FIGS. 4A, 4B, and 4C show the quantification of vascular orientation pattern using orientation, vessel anisotropy, and vessel area.
Figure 4B:
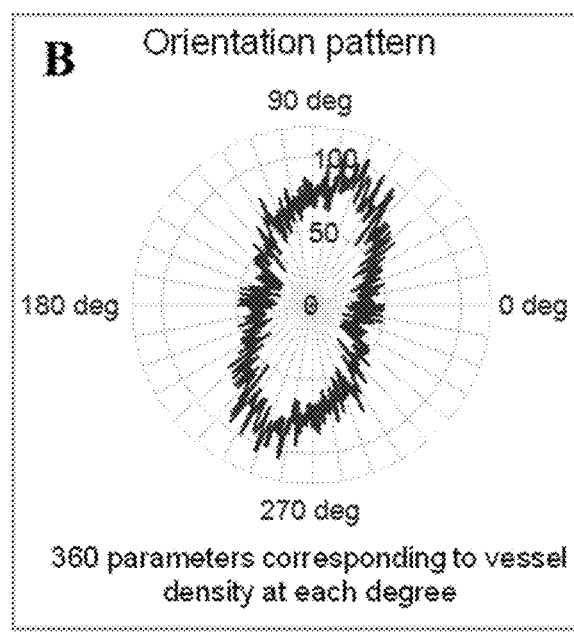
Figure 4C:
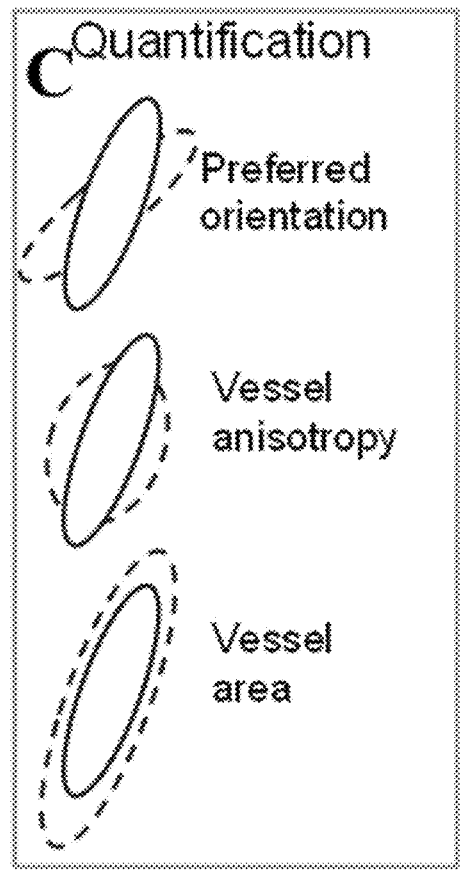
Figure 5A:
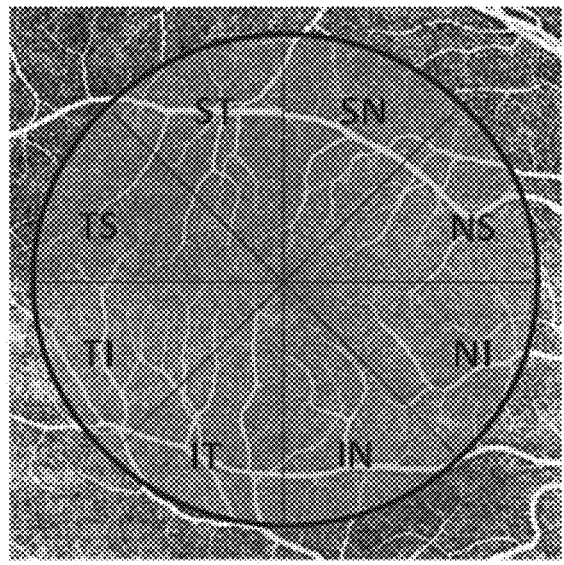
FIGS. 5A, 5B, 5C, 5D, 5E, 5F, 5G, 5H, and 5I show the sectoral vascular pattern with preferred vessel orientation (dashed line) unaligned with sector axis.
Figure 5B:
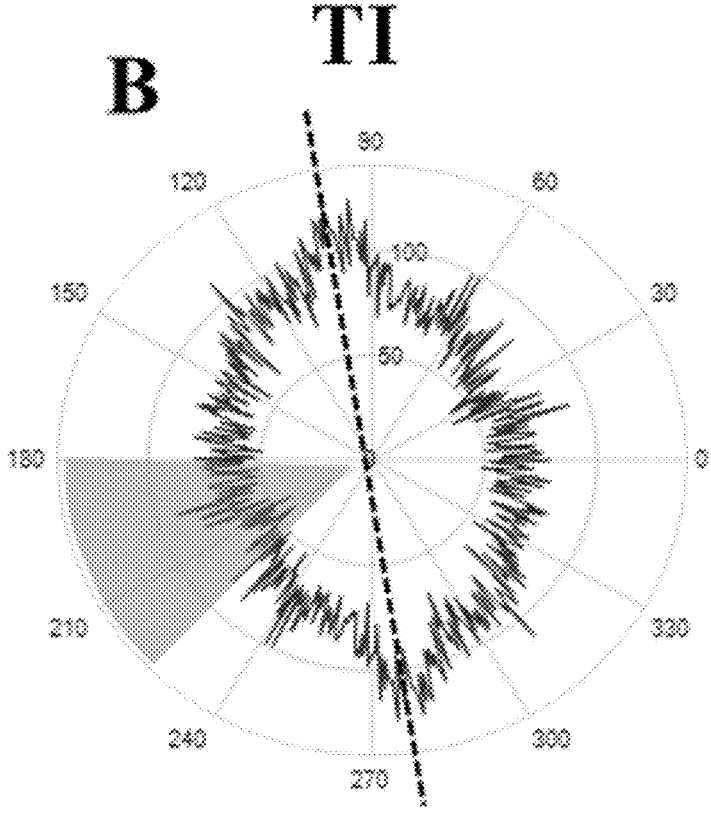
Figure 5C:
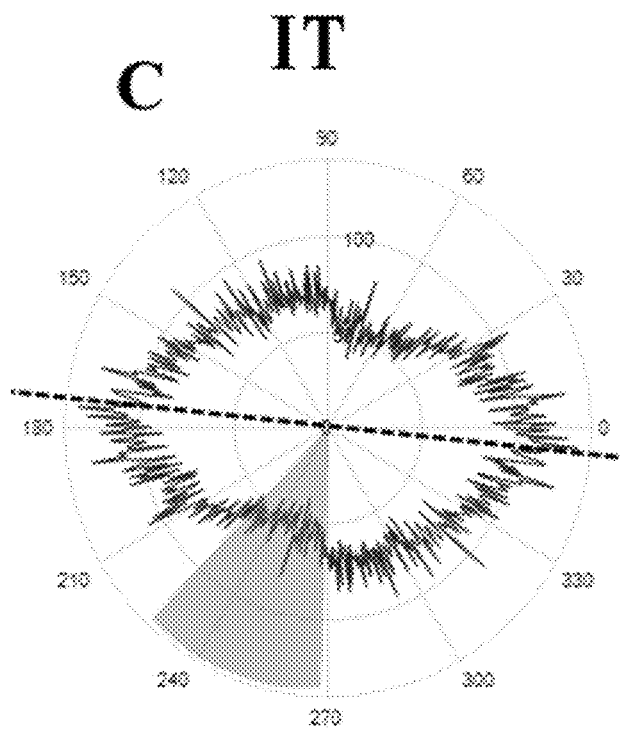
Figure 5D:
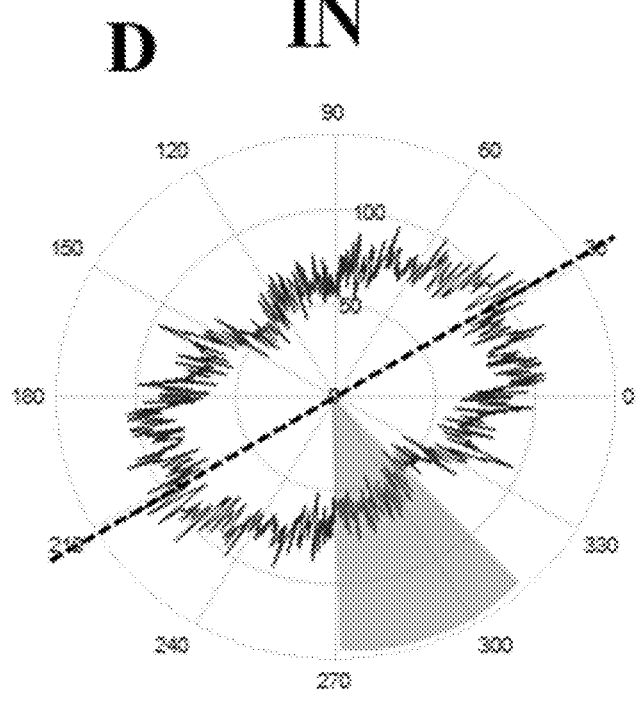
Figure 5E:
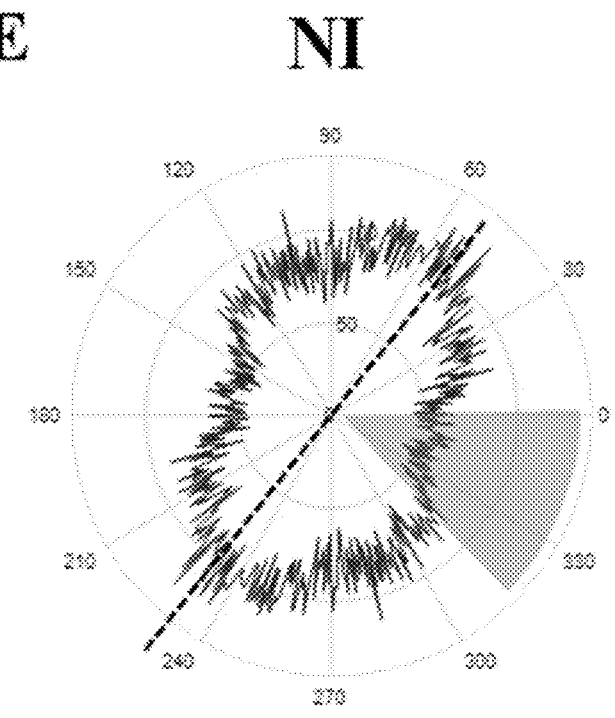
Figure 5F:
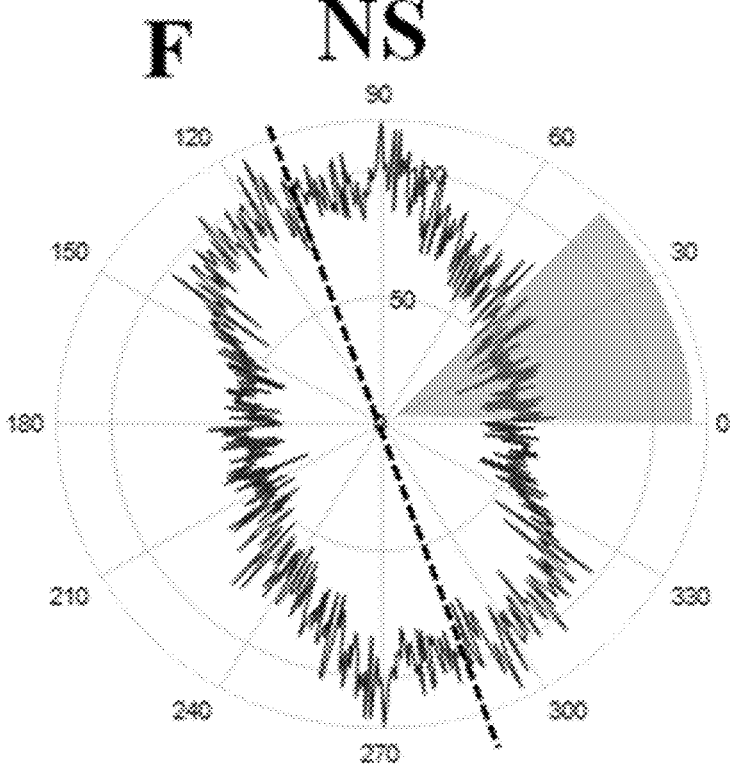
Figure 5G:
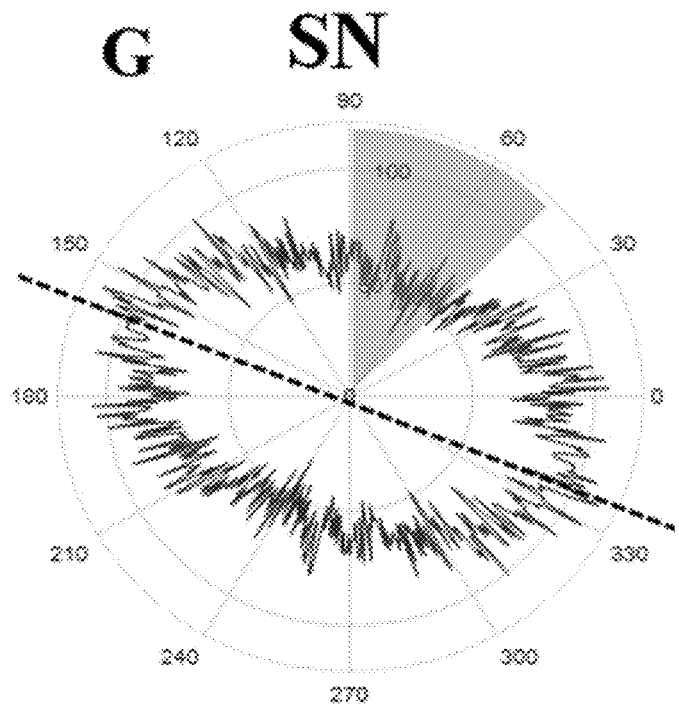
Figure 5H:
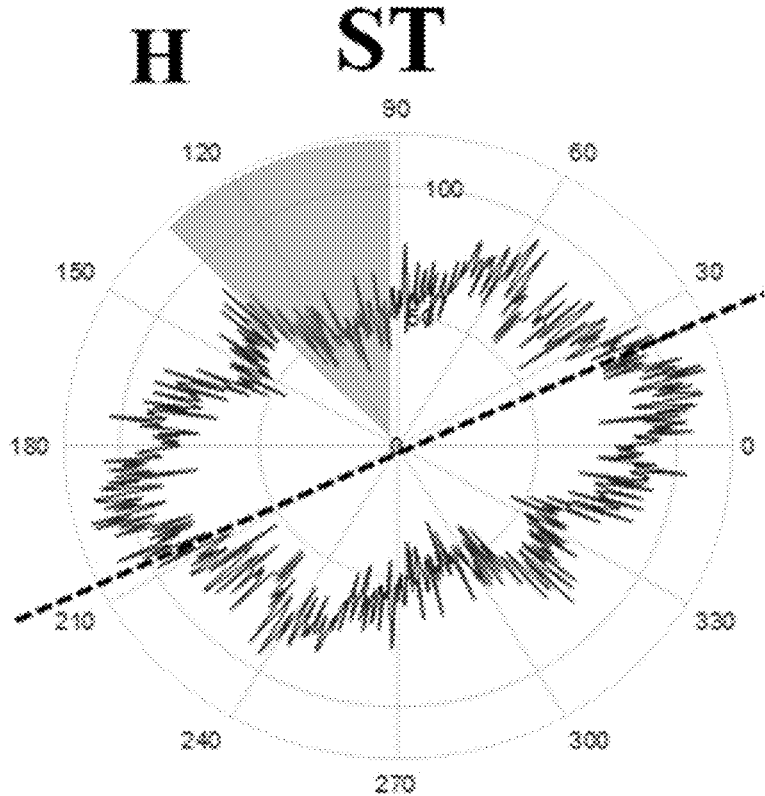
Figure 5I:
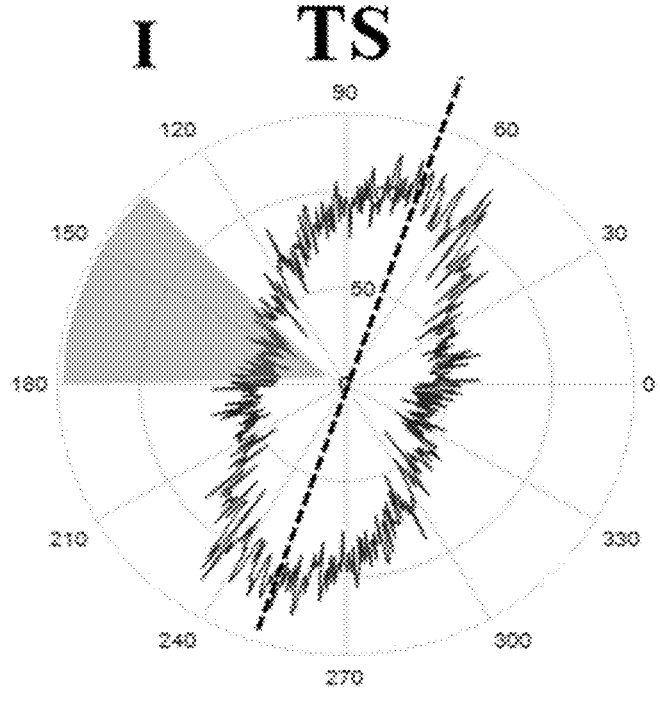

A polar plot of orientation distribution was generated to show the probability of vessel at each angle from 0 to 360 degrees (periodical: n=n+180°). This orientation distribution curve exhibits the unique pattern of vasculature organization in the selected ROI. Quantitative measures of the vessel orientation pattern was achieved by analyzing the polar plot region encompassed by the orientation distribution curve, including preferred orientation, vessel anisotropy, and vessel area. As shown in FIGS. 4A-4C, the orientation pattern for the specific ROI (middle) depicts a roughly elliptical shape with a major axis and a minor axis. The preferred orientation with the unit of degree is identified by the angle of the major axis. The ratio of major axis length and minor axis length is defined as the unitless vessel anisotropy. The vessel area with the unit of pixel$^2$ is defined as the area of the shape or the number of square pixels that covers the closed orientation distribution curve. These three quantitative metrics are independent of each other (FIG. 4C). Descriptive statistics including mean, standard deviation, and range were reported for preferred orientation, vessel anisotropy, and vessel area in each sector of the OCTA image in the healthy and DR cohorts. The statistical analysis was performed by using linear mixed-effect models for analyzing retinal vascular patterns in different sectors of the OCTA image. Non-parametric Mann-Whitney U test (also called Wilcoxon rank sum test) was used to compare the data between DR cases and healthy controls. The correlation between vessel area quantified from the pattern of retinal vascular orientation in the current example and traditionally reported vessel density[24] was evaluated by Pearson correlations. A probability (p) value of 0.05 or less was considered to be statistically significant. All data analysis was conducted by using SAS software (V9.4; SAS Institute Inc., Cary, NC, USA).

Subject Participants

All experiments were performed in adherence to the tenets of the Declaration of Helsinki and informed consent was obtained from all participants. This example was approved by the Institutional Review Board of The Ohio State University. This was a retrospective, cross-sectional, observational example of healthy controls and DR cases. Inclusion criteria for both DR subjects and healthy controls were age 18 years or greater, absence of prior intraocular surgery (except for cataract), corneal pathology and retinal pathology, ability to comprehend, agree, and sign the subject informed consent form, and willingness to comply with the prescribed schedule at the time of enrollment. The disease severity level of the included DR subjects was ranked as mild and moderate (without current evidence of macular edema) based on the modified Airlie House/Early Treatment Diabetic Retinopathy Study (ETDRS). Exclusion criteria for participants included any history of ocular injury and ocular diseases, such as age-related macular degeneration, glaucoma, ocular hypertension, keratoconus, or proliferative diabetic retinopathy. Participants who had a diagnosis of retinal detachment, retinal tear, retinal degeneration, or retinal hole were excluded. Participants were excluded if they were pregnant, less than 12 weeks postpartum, or less than 12 weeks since the last breastfeeding activity. Further, participants with spherical equivalent refraction <−6 diopters or more than +6 diopters were also excluded.

For all participants, OCTA images were acquired with the Spectralis OCTA module (Heidelberg Engineering, Heidelberg, Germany). OCT volume scans centered at the macula were taken with dimensions of 6×6×2 mm consisting of 512 clusters of B-scans with a distance of 11 μm between B-scans. Active eye-tracking (TruTrack) technology was used to correct for displacements by re-acquisition of OCT images at the correct retinal location in real-time. Any images with significant artifactual components due to blockage of OCT signal by floaters and eyelashes, residual motion artifacts, or other artifacts, were excluded from the example to avoid confounding of quantitative analysis. A circular area centered at the macula with a diameter of 5 mm was used (instead of the entire 6×6 mm²) for the aforementioned image processing to reduce the effects of the artifacts at the edge of the scan.

Results

Forty-one subjects were imaged in this example for the quantitative assessment of retinal microvasculature, including 34 healthy controls (age: 21-59 years) and 7 DR cases (age: 24-65 years). Subjects within the healthy and DR cohorts were not significantly different in age (p=0.077). Only one eye (right eye) per subject was included in the analysis.

Figure 6A:
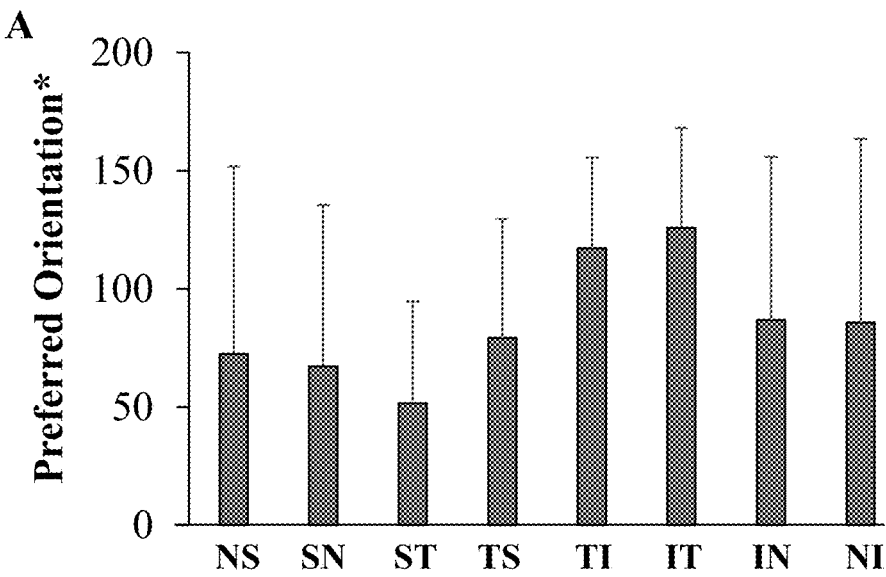
FIGS. 6A, 6B, and 6C show the sectoral difference in retinal microvascular pattern in healthy subjects (n=34). Significant sectoral differences were observed in preferred orientation (FIG. 6A; p<0.0001) and vessel area (FIG. 6C; p<0.0001), whereas vessel anisotropy did not show a significant difference among the 8 sectors (FIG. 6B; p=0.054).
Figure 6B:
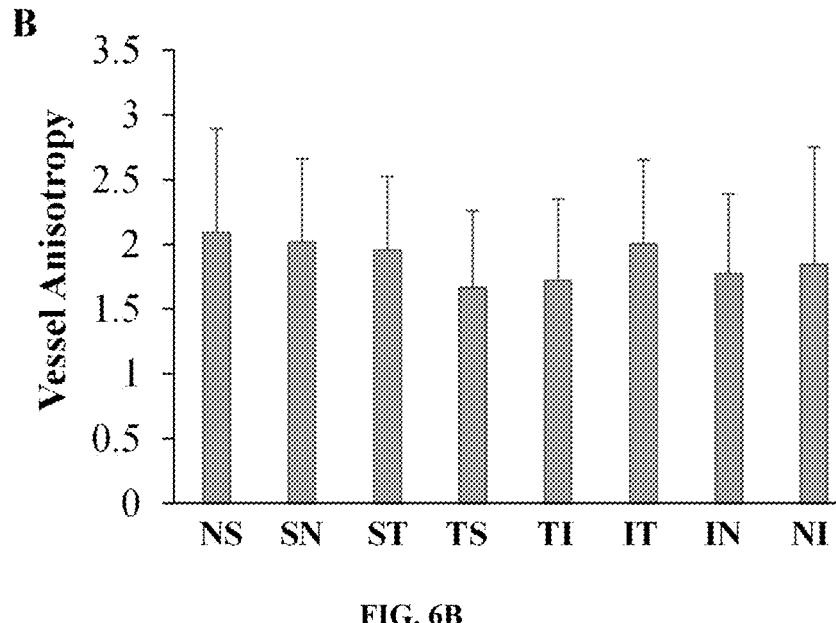
Figure 6C:
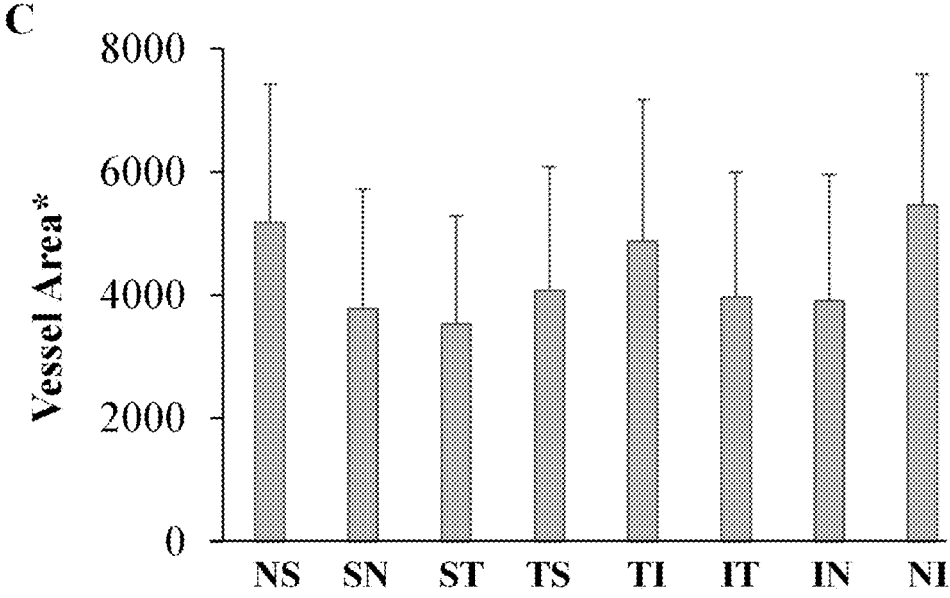

Intra-Subject Sectoral Differences in Retinal Microvascular Orientation Patterns The quantitative analysis defines the ROIs as equal-area sectors. Each 45° sector of the circular disk centered at the macular region was defined as the new ROI, namely NS, SN, ST, TS, TI, IT, IN, and NI (N=nasal, S=superior, T=temporal, I=inferior). The system quantified the vessel orientation pattern for each sectoral ROI, including preferred vessel orientation, vessel anisotropy and vessel area. Analysis shows the preferred vessel orientation of the retinal microvasculature varies within the same eye and is unaligned with their sector axis as shown in FIGS. 5A-5I. The system analyzed the linear mixed model analysis to account for the association of the quantification at different sectors from the same image. Intra-subject sectoral variations were demonstrated in the bar graph for preferred vessel orientation (FIG. 6A), vessel anisotropy (FIG. 6B), and vessel area (FIG. 6C). In the healthy cohort, significant differences were observed among the 8 sectors in preferred vessel orientation (p<0.0001) and vessel area (p<0.0001), while no significant sectoral difference was observed in vessel anisotropy (p=0.054).

Figure 7:
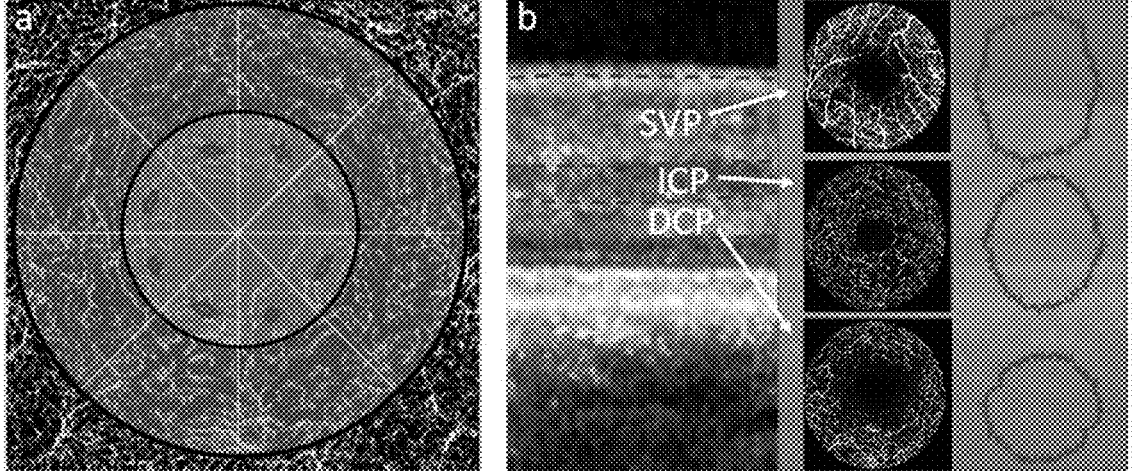
FIG. 7 shows the three-dimensional mapping of the vessel orientation pattern which exhibits variance in different sectors, inner vs outer (a), and in different layers (b). SVP=superficial vascular plexus; ICP=intermediate capillary plexus; DCP=deep capillary plexus

Note that the quantification in this example focused on 8 sectoral ROIs from the full projection of the OCTA image (summing up all the retina layers in the thickness direction). The present software operation in ROI selection can be performed with more refined regions from a volumetric vasculature. FIG. 7 shows a three-dimensional mapping of the vessel orientation pattern which exhibits variance in different sectors, inner vs outer (a), and in different layers (b). SVP=superficial vascular plexus; ICP=intermediate capillary plexus; DCP=deep capillary plexus. For each 3D macular scan, the vessel orientation pattern can be mapped in three layers: SVP, ICP, and DCP; for each layer, map the vessel orientation patterns can be mapped in 16 ROIs segmented by radius and theta, namely, NI_inner, IN_inner, NS_inner, SN_inner, TI_inner, IT_inner, TS_inner, ST_inner, NI_outer, IN_outer, NS_outer, SN_outer, TI_outer, IT_outer, TS_outer, ST_outer.

Differential Retinal Microvascular Orientation Patterns Between Healthy and DR Cohorts In the SN and ST sectors, the average preferred vessel orientation of healthy subjects was similar to that of DR subjects (SN: 67.2°±68.4° for healthy vs 62.2°±77.10 for DR; ST: 51.7°±43.10 for healthy vs 49.4°±31.2° for DR). The largest difference in preferred orientation between healthy and DR was observed in the IN sector (86.8°±69.10 for healthy vs 157.2°±29.4° for DR, p=0.005). It is worth noting that due to the head-tail nature of the preferred orientation, i.e., 0° and 180° define the same line direction, when the standard deviation in a certain sector for healthy or DR subjects is greater than 45°, the preferred orientation for some subjects falls into the first quadrant closer to 0° and some fall into the second quadrant closer to 180° (see Table 1). For the vessel anisotropy, no significant difference was observed in any of the 8 sectors between healthy and DR cohorts. The average vessel area in DR is smaller than healthy subjects in the TI and IT sectors (TI: 4879±2297 pixel² for healthy vs 2277±1464 pixel² for DR, p=0.004; IT: 3967±2025 pixel² for healthy vs 2420±1592 pixel² for DR, p=0.046).

Table 1 lists the quantification of retinal microvascular patterns for healthy and DR subjects including the average, standard deviation, and the range for each metric in each sector. Asterisk indicates statistical significance at the level of 0.05 using the non-parametric Mann-Whitney U test for the comparison of DR and healthy subjects.

Comparison between Vascular Orientation Pattern and Vessel Density

Figure 8A:
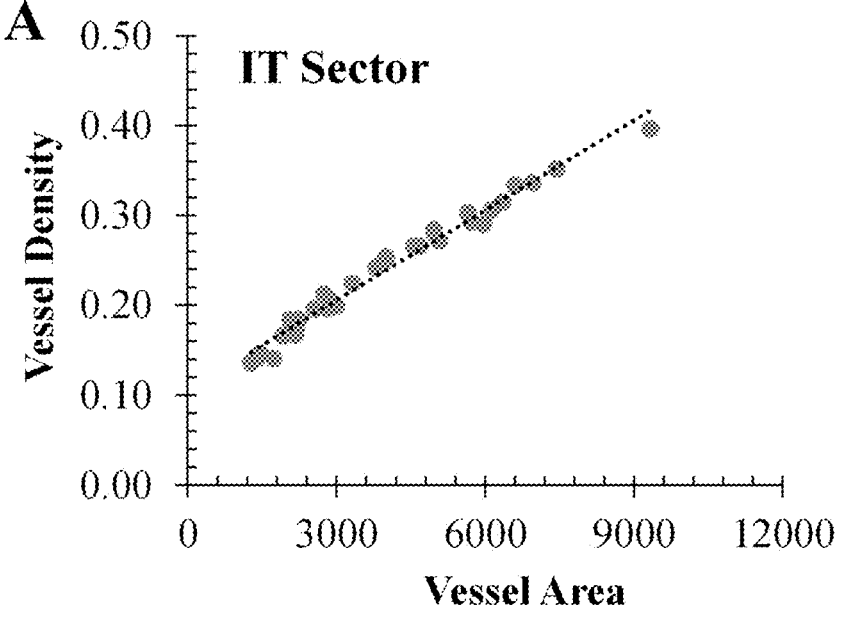
FIGS. 8A and 8B show the scatterplots of the relationship between vessel area and vessel density.
Figure 8B:
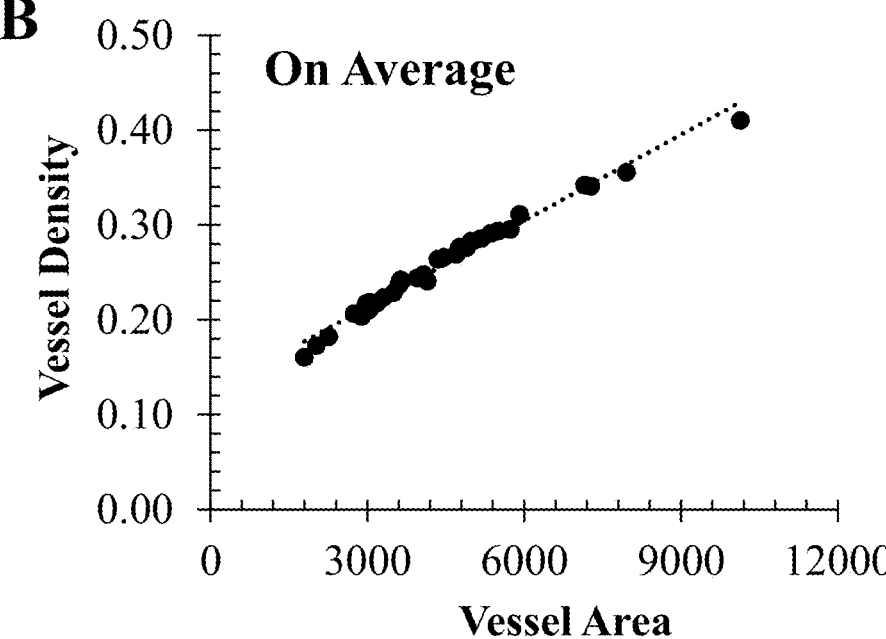
Figure 9A:
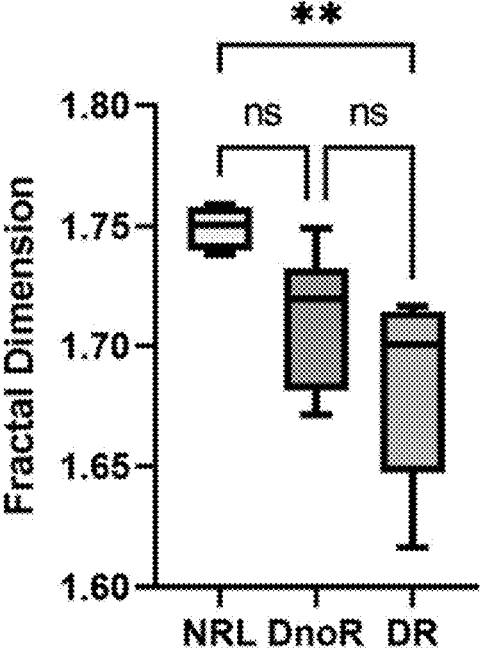
FIGS. 9A, 9B, 9C, and 9D show fractional dimension between subjects that are diabetic without retinopathy (DnoR), diabetic retinopathy (DR), and normal controls (NRL).
Figure 9B:
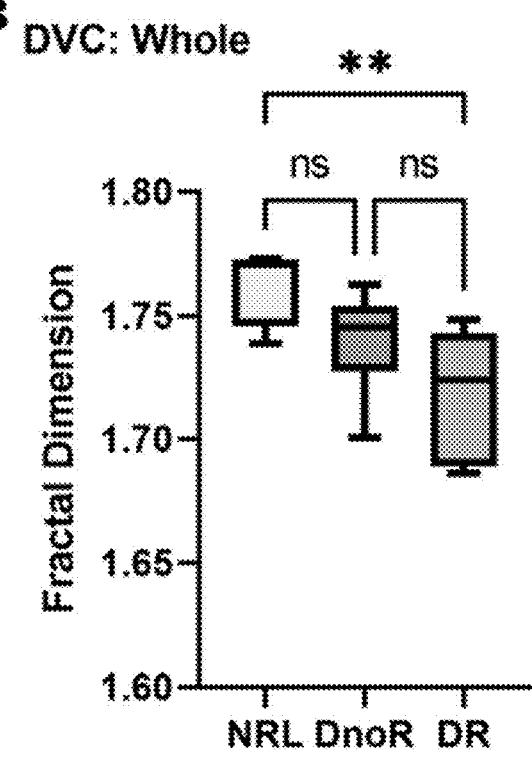
Figure 9C:
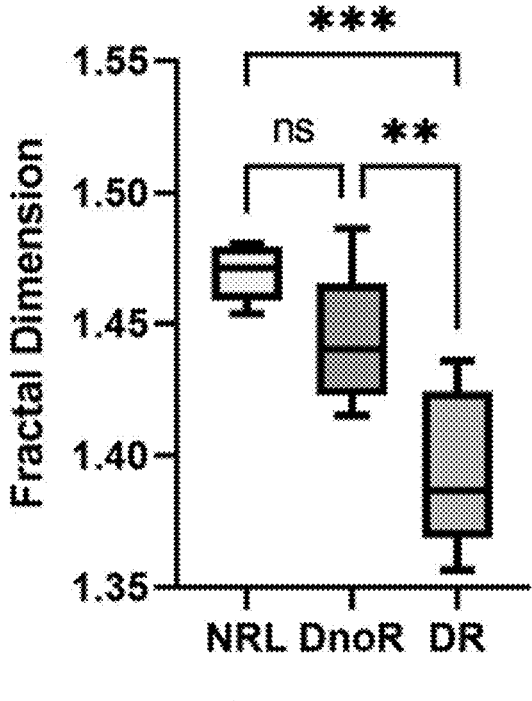
Figure 9D:
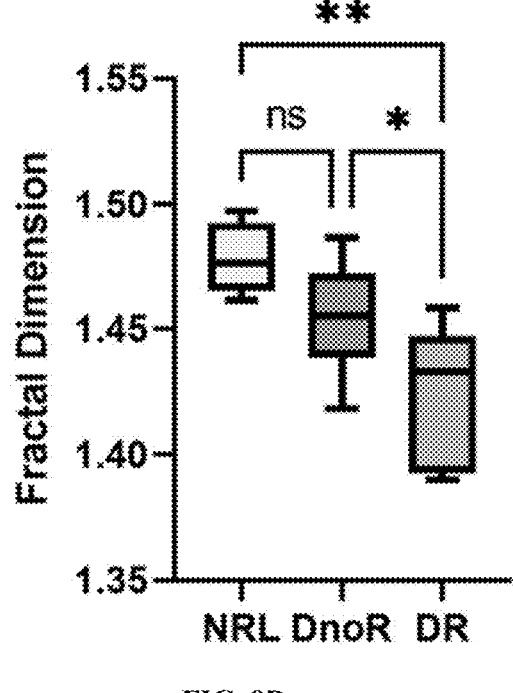
Figure 10A:
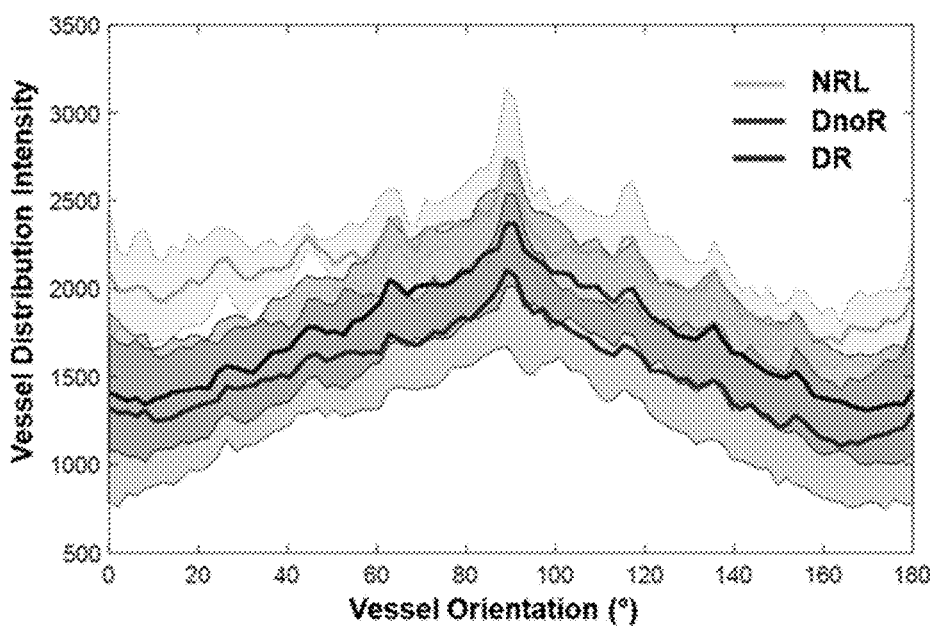
FIGS. 10A, 10B, 10C, and 10D show the different vascular orientation pattern curves among DnoR, DR, and NRL in different ROIs.
Figure 10B:
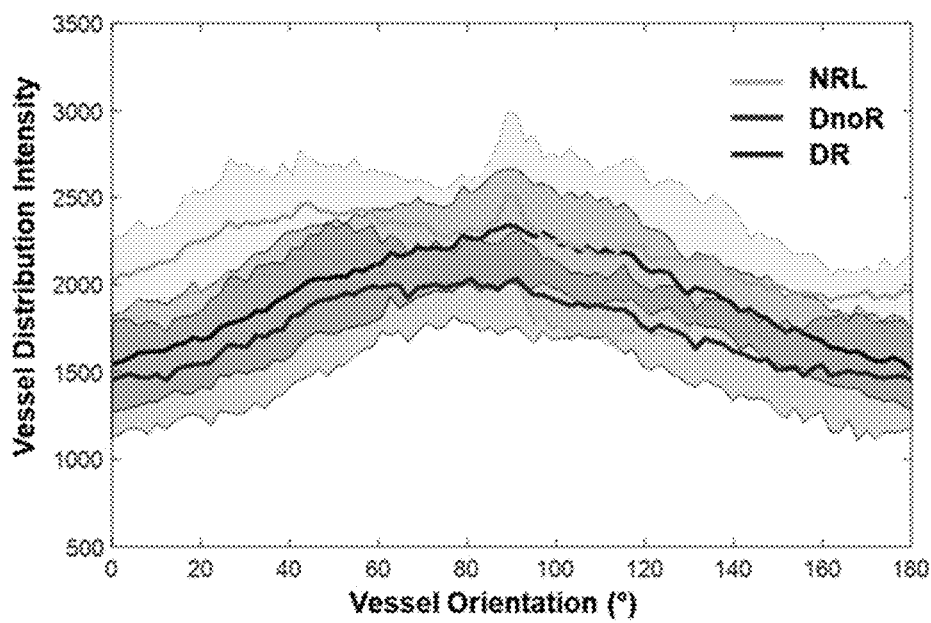
Figure 10C:
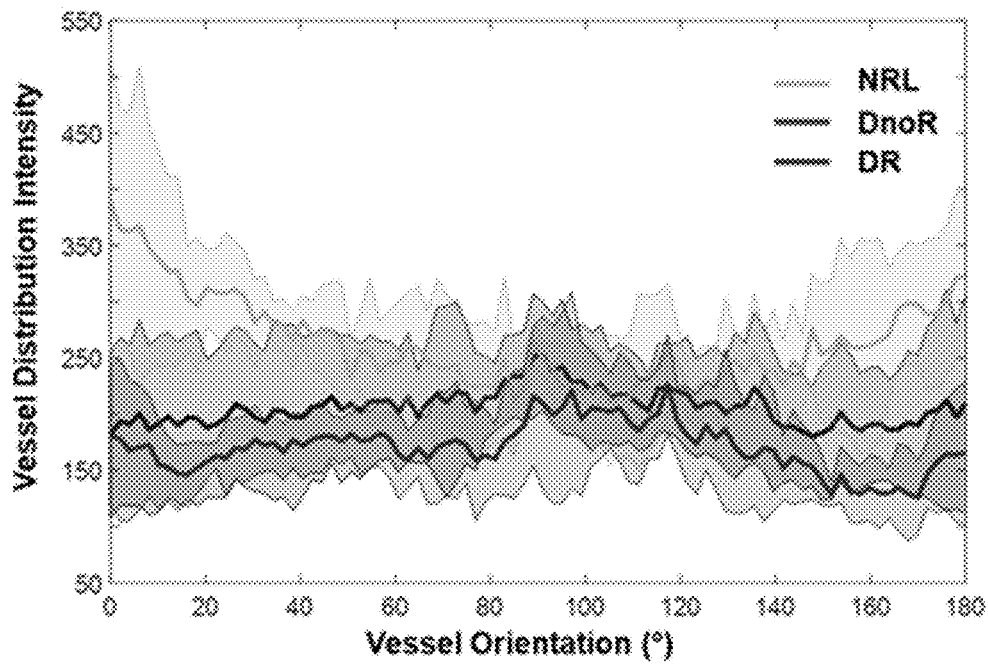
Figure 10D:
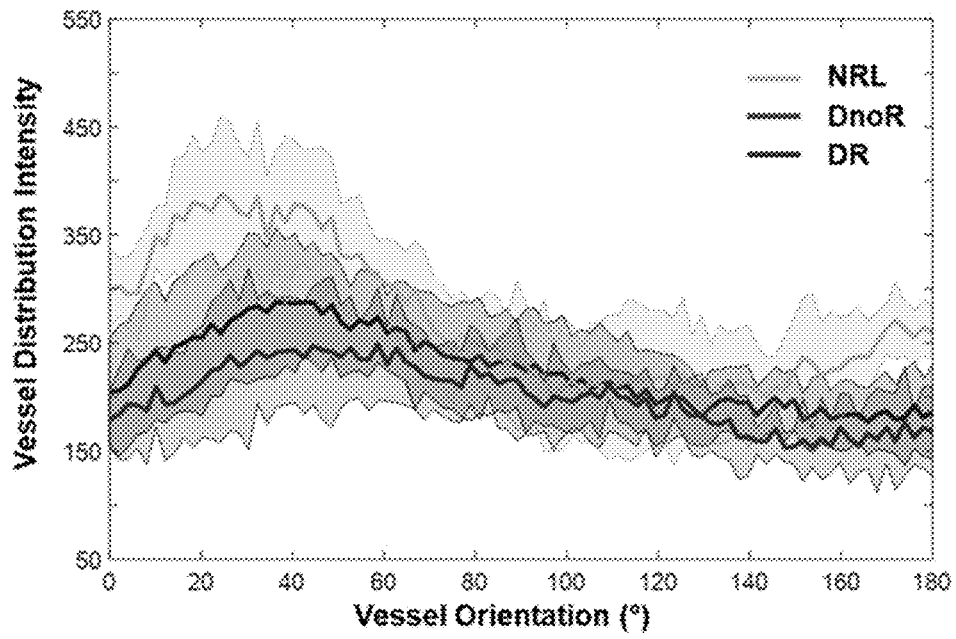

Vessel density was calculated as the ratio of the vasculature to the total image area in the ROI in the binary vessel map. The vessel area and the vessel density were compared in 34 healthy subjects in each sector. The vessel density and vessel area were strongly correlated with Pearson R>0.97 at every sector (p<0.0001 for all 8 sectors). In addition, since our quantitative analysis defines the ROIs as equal-area sectors, the mean value of vessel density in the 8 sectors represents the overall density in the circular disk centered at the macula. The averaged vessel density and averaged vessel area in the 8 sectors were also strongly correlated (R=0.99, p<0.0001). FIGS. 8A-8B provides scatterplots of the relationship between vessel area and vessel density in the IT sector and on average. Our quantitative analysis for vascular orientation pattern not only provides vessel area, but also preferred orientation and vessel anisotropy simultaneously, demonstrating its advantage as a quantitative tool over vessel density alone.

Discussion

The pathologic mechanism of DR is directly related to the underlying hyperglycemia associated with diabetes. The best way to prevent or delay the progression of DR is early and aggressive control of one's blood sugar. Hemoglobin A1c remains the only confirmed systemic prognostic bio-marker of DR progression. However, the fact that diabetics with appropriate glycemic control still develop vision loss exemplifies the need for additional markers of DR onset and progression. In the early stage of DR, patients are generally asymptomatic. Ophthalmic imaging acquired from the patient's routine eye examination offers a way to identify and track the cumulative damage from hyperglycemia. Thus, advanced image-based quantification has valuable information and provides more efficient management of the patient with DR. Several quantitative metrics using en face OCTA images have been developed to objectively characterize the retinal vessels with the objective of detecting or staging DR. Vessel density over a desired region of interest is the most common quantitative assessment made with OCTA. Although vessel density measurements showed statistically significant differences between the DR and healthy eyes, it had limited sensitivity to detect DR at early stage. Measurements of the vessel density using OCTA showed relatively good repeatability for various retinal diseases including diabetic macular edema, retinal vein occlusion with macular edema, epiretinal membrane, and wet age-related macular degeneration. However, the decrease in vessel density was not only observed in DR, but also in other retinal disease, showing poor specificity for DR detection using vessel density. Noting the limitation of vessel density as a quantitative metric to characterize DR-associated changes in retinal microvasculature, automatic segmentation algorithms have been developed to extract vascular features such as geometric perfusion deficits, foveal avascular zone, intercapillary area, and fractal dimension. In this example, a quantitative approach to delineate the pattern of retinal vascular orientation was developed from OCTA images which generated three quantitative metrics. First, Gaussian multi-scale convolution was combined with the second derivative to tune the vesselness filter response to the specific vessel width and orientation. Then with the identification of vessel orientation at each pixel, the pixels at a certain angle ranging from 0 to 360 degrees were integrated, which yielded the orientation pattern in the desired ROI. Preferred vessel orientation, vessel anisotropy, and vessel area were defined to quantify the orientation pattern, reducing 360 descriptive metrics to a manageable three metrics. These results have elucidated that this quantitative approach is more advanced than the traditionally reported vessel density in two aspects:

(1) Extra metrics were achieved by quantifying the vessel orientation pattern beyond a single quantitative analysis of vessel density. The vessel area characterized from the vascular orientation pattern was shown to be strongly correlated with the traditionally reported vessel density. Quantification of vessel preferred orientation and anisotropy that were characterized from the vascular orientation pattern simultaneously along with vessel area provides additional information about the retinal vasculature. Thus, this vessel orientation-based quantitative assessment for retinal microvasculature provides for DR detection at the earliest stage.

(2) Sectoral analysis for the retinal vasculature presents the development of a biomarker for the DR disease. In this example, a circular area centered at the macula with a diameter of 5 mm (from 6×6 OCTA image) was used to allow an anatomically more consistent comparison among subjects, and to reduce the effects of the artifacts at the edge of the scan. Eight 45° sectors of the circular disk were defined as the ROI. Significant sectoral differences were observed in preferred vessel orientation (p<0.0001) and vessel area (p<0.0001) in the healthy controls. Further, vessel preferred orientation and vessel area quantified from the vascular orientation pattern also demonstrated a difference between healthy and DR cohorts in certain sectors. The sectoral analysis therefore shows better performance in identifying focal defects manifested in DR.

The methods disclosed herein focus on the development with proof-of-concept results on the differential retinal microvascular orientation patterns between healthy and DR subjects to demonstrate the feasibility and advantage of this approach. The quantification in this example focused on the full projection of the OCTA image (summing up all the retina layers in the thickness direction). Quantification of the retinal vascular pattern within different layers to further analyze the regional difference can also be done. Another application of the retinal microvascular orientation is to evaluate the tortuosity in vessels recognized in digital fundus images or OCTA images. Tortuosity is one of the first alterations in the retinal vasculature in hypertensive retinopathy. For instance, hypertensive patients have severe vessel tortuosity compared to healthy subjects who exhibit normal/very mild vessel tortuosity.

In conclusion, this quantitative approach using OCTA imaging allows for the mapping and quantification of the retinal microvascular orientation pattern, which in turn holds shows use for the early detection of DR-associated retinal vascular abnormalities.

Example 2: Multi-Dimensional Quantification of Diabetic Retinopathy Early Detection Disclosed herein are methods to extract vascular features in the superficial (SVC) and deep (DVC) vascular complex using optical coherence tomography angiography (OCTA). They are compared among subjects with mild to moderate diabetic retinopathy without macular edema (DR), diabetics without retinopathy (DnoR), and normal controls (NRL).

Methods 20 participants were included with 10 DnoR (age: 32-72 years), 5 NRL (age: 23-42 years) and 5 DR (age: 42-85 years). One eye (OD) per subject was analyzed. OCTA images were acquired with the Spectralis (Heidelberg Engineering, Heidelberg, Germany) centered at the 3×3 mm$^2$ macular region. The quantification defines the region of interests (ROIs) as 450 equal-area sectors namely NS, SN, ST, TS, TI, IT, IN, and NI (N=nasal, S=superior, T=temporal, I=inferior), in addition to the whole circular zone centered at the macula.

The microvascular morphologic features were analyzed using fractal dimension (FD) and vascular orientation pattern curve. FD is a metric to characterize global vessel anatomical complexity. Vascular orientation pattern captures local variations in the vessel orientation ranging from 0 to 180°, and the area under the curve indicates the vessel area density (VAD).

An analysis of variance (ANOVA) and post hoc Tukey's test was performed to detect the difference in FD and VAD in each ROI among the three groups.

Results

Tukey's multiple comparisons test to compare the FD and VAD for each of the sectors in the SVC and DVC among the three groups are given in Tables 2 and 3. For the whole macular zone, significant differences in FD and VAD were observed between NRL and DR. Sector IN showed significant difference not only between NRL and DR, but also between DnoR and NRL in VAD (p=0.006 for SVC; p=0.022 for DVC), and between DnoR and DR in FD (p=0.003 for SVC; p=0.040 for DVC) (see FIGS. 9A-9D). Compared to analyzing the whole macular zone, the vascular orientation pattern in DR shows greater difference from NRL or DnoR in sector IN (see FIGS. 10A-10D).

Conclusions

Retinal vascular features were extracted from OCTA images for multi-dimensional quantification using layer- and sector-based ROIs. Vascular orientation pattern curve provides a clear presentation of the spatial distribution of vessels with more information than a global metric such as vessel density. DR-associated microvascular deterioration is not uniform in all sectors. Different sectoral ROIs exhibited different abilities to differentiate DR from the DnoR or NRL. Sector IN detected the microvascular difference between DnoR and DR, and its sectoral analysis holds promise for DR detection at the earliest stage.

Figure 11A:
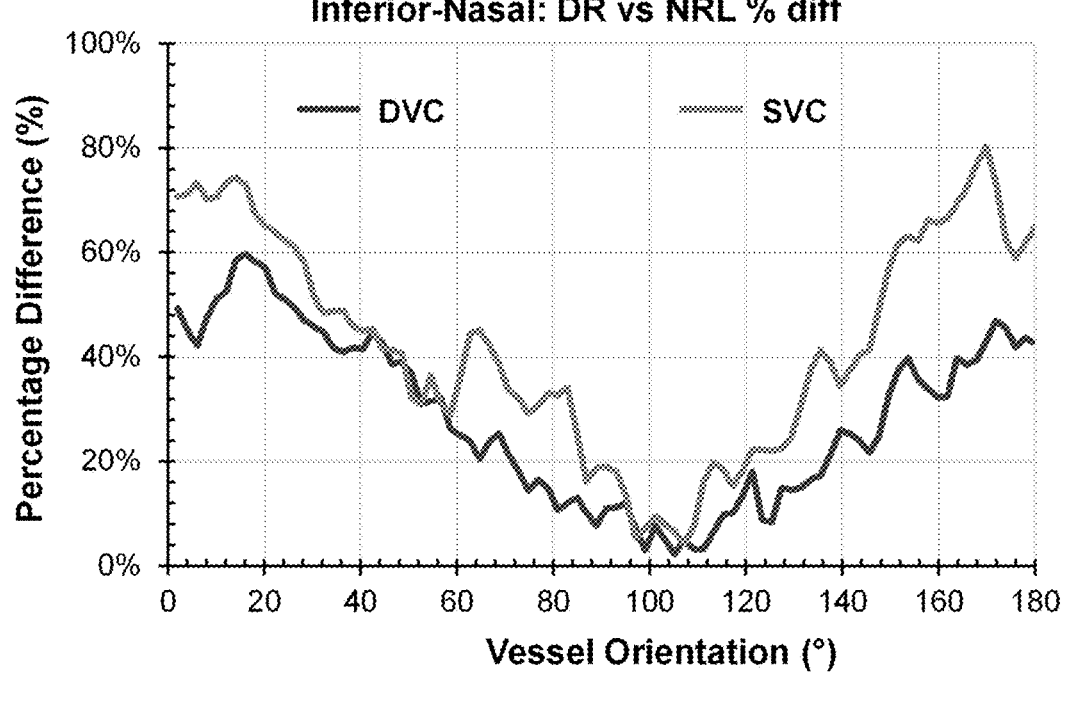
FIGS. 11A and 11B show the difference in vascular orientation distribution between normal subjects (NRL) and diabetic retinopathy (DR).

Example 3: Determining Percentage Difference in Vessel Orientation Distribution in Patients with DR The present example provides quantitative vessel deterioration defined by the percentage difference in the vessel probability at each vessel orientation between disease and normal controls. DR-associated microvascular deterioration is not uniform in all sectors nor all orientations. For instance, in the sector inferior-nasal (IN), between normal and DR the average percentage difference for vessels aligned in 0-20 degrees was 52.15% for DVC and 70.80% for SVC, while the average percentage difference for vessels aligned in 80-100 degrees was 9.65% for DVC and 17.97% for SVC. See FIG. 11A.

Note: percentage difference equals the absolute value of the change in value, divided by the average of the 2 numbers, all multiplied by 100. The percent sign, %, is appended to designate the % difference.

Figure 11B:
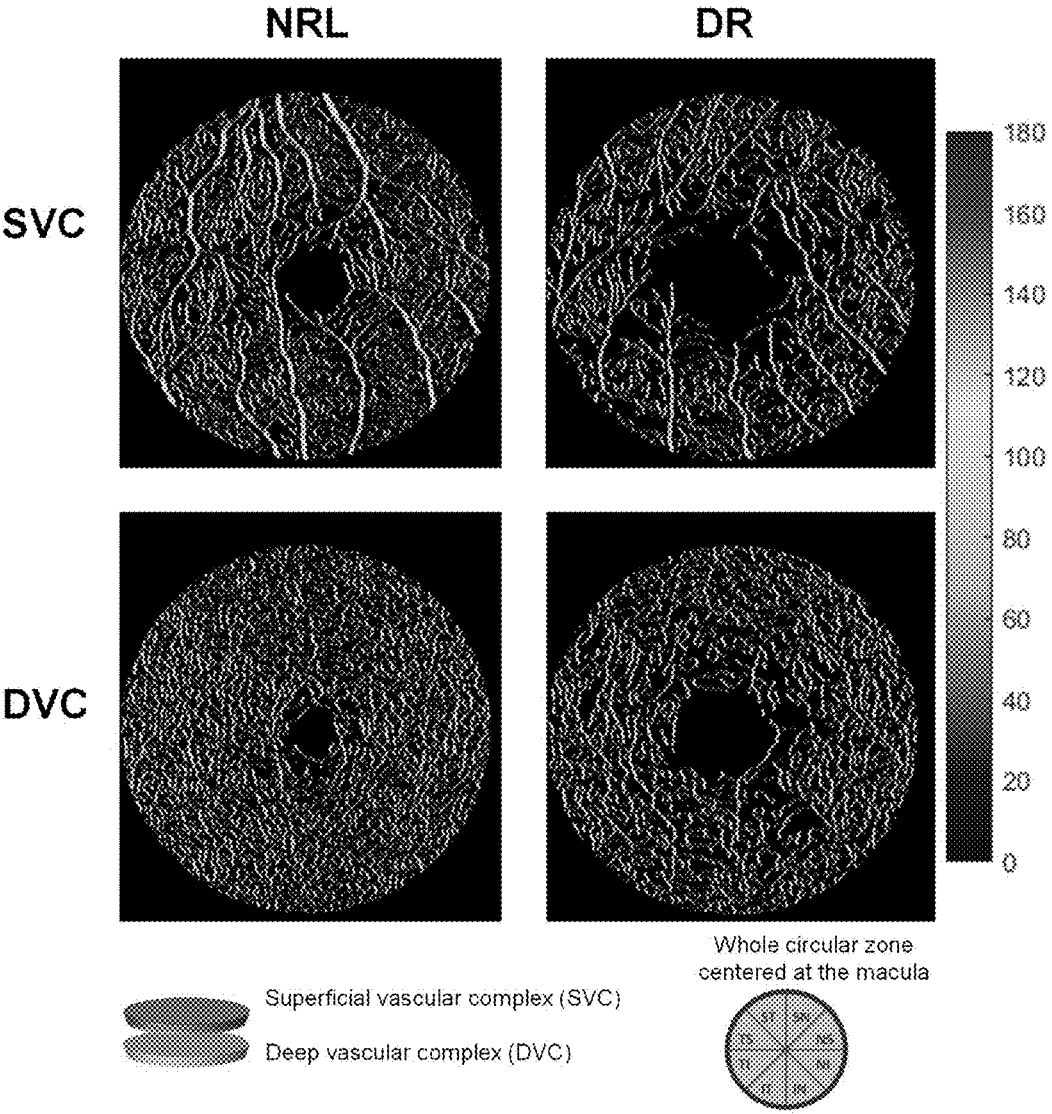

Following the calculation on the percentage difference in vessel probability between NRL and DR which can be used to indicate vessel deterioration, a color map can be generated showing the retinal vascular orientation distribution. FIG. 11B shows an example color map that can be used to assist in the interpretation and understanding of the aspects of informing ocular disease diagnosis, monitoring, and treatment using the present invention.

As shown in the example color map of FIG. 11B, it can be observed that in this sector data (i.e., IN sector), the large vessels are mostly in between the 80° and 120° range, and those large vessels are less susceptible to damage which may explain why the difference is low for vessels aligned in 80-120 degrees. It has been further observed from the study reported therein that the big difference in vessels aligned between 0° and 20° or between the 160° and 180° may indicate that the capillary dropout occurs mostly first on the vessels that are aligned perpendicular to the large vessels. This map can demonstrate the advantage and uniqueness of the exemplary method in understanding vascular development or remodeling in ocular disease.

In the orientation map, the dark blue and red colors indicate 0° and 180°, respectively, for the horizontal vessels and the green color indicates 90° for those vertical vessels. The IN region (in this example) is quite blue in the NRL compared to DR.

It will be apparent to those skilled in the art that various modifications and variations can be made in the present disclosure without departing from the scope or spirit of the invention. Other embodiments of the disclosure will be apparent to those skilled in the art from consideration of the specification and practice of the methods disclosed herein. It is intended that the specification and examples be considered as exemplary only, with a true scope and spirit of the invention being indicated by the following claims.

Tables

TABLE 1

Quantification of retinal microvascular pattern for 34 healthy and 7 DR subjects, including the average value, standard deviation and range for preferred orientation (A), vessel anisotropy (B), and vessel area (C) in each sector.

| A. Preferred Orientation (°) | Healthy (n = 34) | | | Diabetic Retinopathy (DR, n = 7) | | |
|---|---|---|---|---|---|---|
| | Mean ± SD | Mini-mum | Maxi-mum | Mean ± SD | Mini-mum | Maxi-mum |
| NS | 72.5 ± 79.2 | 0.5 | 178.7 | 38.3 ± 59.6 | 3.9 | 168.6 |
| SN | 67.2 ± 68.4 | 1.5 | 175.2 | 62.2 ± 77.1 | 2.1 | 178.2 |
| ST | 51.7 ± 43.0 | 1.3 | 177.2 | 49.4 ± 31.2 | 15.8 | 105.2 |
| TS | 79.3 ± 50.3 | 0.4 | 177.9 | 92.4 ± 53.5 | 2.7 | 158.7 |
| TI | 117.2 ± 38.3 | 5.2 | 178.7 | 86.7 ± 60.7 | 1.6 | 158.8 |
| IT | 125.9 ± 42.3 | 5.9 | 176.2 | 137.1 ± 22.0 | 103.5 | 167.9 |
| IN* | 86.8 ± 69.1 | 1.4 | 174.8 | 157.2 ± 29.4 | 109.6 | 179.5 |
| NI | 85.8 ± 77.6 | 0.6 | 179.8 | 145.0 ± 62.8 | 3.3 | 179.5 |

| B. Vessel Anisotropy | Healthy (n = 34) | | | Diabetic Retinopathy (DR, n = 7) | | |
|---|---|---|---|---|---|---|
| | Mean ± SD | Mini-mum | Maxi-mum | Mean ± SD | Mini-mum | Maxi-mum |
| NS | 2.1 ± 0.8 | 1.2 | 4.5 | 1.9 ± 0.3 | 1.5 | 2.4 |
| SN | 2.0 ± 0.6 | 1.1 | 3.7 | 2.5 ± 1.4 | 1.5 | 5.1 |
| ST | 2.0 ± 0.6 | 1.3 | 4.1 | 1.7 ± 0.5 | 1.2 | 2.4 |
| TS | 1.7 ± 0.6 | 1.0 | 3.8 | 1.8 ± 0.7 | 1.1 | 2.8 |
| TI | 1.7 ± 0.6 | 1.0 | 3.7 | 2.4 ± 0.9 | 1.1 | 3.7 |
| IT | 2.0 ± 0.6 | 1.0 | 3.6 | 2.0 ± 0.8 | 1.3 | 3.4 |
| IN | 1.8 ± 0.6 | 1.0 | 4.0 | 1.9 ± 0.6 | 1.1 | 2.6 |
| NI | 1.8 ± 0.9 | 1.2 | 5.2 | 1.9 ± 0.5 | 1.2 | 2.6 |

31

TABLE 1-continued

| C. Vessel | Healthy (n = 34) | | | Diabetic Retinopathy (DR, n = 7) | | |
|---|---|---|---|---|---|---|
| Area (pixel$^2$) | Mean ± SD | Mini-mum | Maxi-mum | Mean ± SD | Mini-mum | Maxi-mum |
| NS | 5182 ± 2240 | 2226 | 10824 | 4988 ± 1922 | 1885 | 7470 |
| SN | 3769 ± 1952 | 1498 | 9884 | 3433 ± 1183 | 1815 | 5061 |
| ST | 3525 ± 1754 | 1273 | 8832 | 2631 ± 1281 | 854 | 3903 |
| TS | 4072 ± 2012 | 1355 | 11171 | 2966 ± 1762 | 1040 | 5403 |
| TI* | 4879 ± 2297 | 1379 | 10486 | 2277 ± 1464 | 652 | 5160 |
| IT* | 3967 ± 2025 | 1274 | 9331 | 2420 ± 1592 | 736 | 5063 |
| IN | 3896 ± 2063 | 842 | 10028 | 2345 ± 1835 | 455 | 4972 |
| NI | 5461 ± 2125 | 2072 | 11353 | 4735 ± 3001 | 1145 | 9605 |

Asterisk * indicates statistically significant (p < 0.05 between healthy and DR cohorts using Mann-Whitney U test. SD ± standard deviation.

TABLE 2

Multiple Comparison Tests for Fractal Dimension

| | Superficial Vascular Complex (SVC) | | | Deep Vascular Complex (DVC) | | |
|---|---|---|---|---|---|---|
| | NRL vs DnoR | NRL vs DR | DnoR vs DR | NRL vs DnoR | NRL vs DR | DnoR vs DR |
| Whole | 0.078 | 0.005 | 0.182 | 0.143 | 0.008 | 0.146 |
| NS | 0.148 | 0.157 | 0.962 | 0.083 | 0.102 | 0.972 |
| SN | 0.232 | 0.059 | 0.495 | 0.318 | 0.038 | 0.262 |
| ST | 0.188 | 0.137 | 0.874 | 0.465 | 0.154 | 0.558 |
| TS | 0.389 | 0.029 | 0.162 | 0.575 | 0.076 | 0.239 |
| TI | 0.383 | 0.014 | 0.079 | 0.691 | 0.063 | 0.143 |
| IT | 0.993 | 0.185 | 0.137 | 0.635 | 0.040 | 0.105 |
| IN | 0.121 | 0.000 | 0.003 | 0.152 | 0.002 | 0.040 |
| NI | 0.129 | 0.003 | 0.070 | 0.423 | 0.041 | 0.204 |

Bolded values indicate statistical significance (p < 0.05)

TABLE 3

Multiple Comparison Tests for Vessel Area Density

| | Superficial Vascular Complex (SVC) | | | Deep Vascular Complex (DVC) | | |
|---|---|---|---|---|---|---|
| | NRL vs DnoR | NRL vs DR | DnoR vs DR | NRL vs DnoR | NRL vs DR | DnoR vs DR |
| Whole | 0.026 | 0.002 | 0.237 | 0.108 | 0.009 | 0.217 |
| NS | 0.089 | 0.050 | 0.770 | 0.101 | 0.067 | 0.823 |
| SN | 0.114 | 0.032 | 0.529 | 0.356 | 0.044 | 0.263 |
| ST | 0.132 | 0.104 | 0.885 | 0.526 | 0.170 | 0.534 |
| TS | 0.297 | 0.028 | 0.217 | 0.555 | 0.103 | 0.330 |
| TI | 0.149 | 0.007 | 0.121 | 0.526 | 0.059 | 0.211 |
| IT | 0.115 | 0.011 | 0.243 | 0.307 | 0.030 | 0.224 |
| IN | 0.006 | 0.000 | 0.100 | 0.022 | 0.002 | 0.270 |
| NI | 0.009 | 0.003 | 0.560 | 0.062 | 0.019 | 0.557 |

Bolded values indicate statistical significance (p < 0.05)

The following patents, applications, and publications, as listed below and throughout this document, describes various application and systems that could be used in combination the exemplary system and are hereby incorporated by reference in their entirety herein.

[1] Ma, Y. H. et al. Quantifying the pattern of retinal vascular orientation in diabetic retinopathy using optical coherence tomography angiography. Sci. Rep. 11, 15826 (2021).

What is claimed is:

1. A method for treating an ocular vascular disease in a patient in need thereof, the method comprising:

extracting a retinal vascular feature from a set of images acquired by an imaging modality and obtained from the patient to provide to a computer software;

carrying out a multi-dimensional quantification comprising layer- and sector-based regions of interest via the computer software to generate a collection of vascular orientation pattern curves;

analyzing the vascular orientation pattern curves via a trained AI model of the computer software;

placing the patient into a group based on the analysis of the vascular orientation pattern curve of the patient, wherein said groups comprise: i. a normal range, ii. mildly abnormal range, and iii. a severely abnormal range;

selecting the patient from group ii for further monitoring, and selecting the patient from group iii for treatment, wherein the trained AI model is configured to:

receive a data set comprising ocular or retinal vascular image or object;

determine a set of orientation vectors at each pixel, or a set of pixels, of a set of pre-defined regions of the ocular or retinal vascular image or object, including a first region and a second region;

determine a set of first quantification metrics from the set of orientation vectors for the first region; and determine a set of second quantification metrics from the set of orientation vectors for the second region, wherein the first and second sets of quantification metrics are employed in a diagnosis or a treatment of an ocular or retinal vascular disease.

2. The method of claim 1, wherein the ocular vascular disease is a retinal vascular disease.

3. The method claim 2, wherein the retinal vascular disease is selected from any one of the groups consisting of diabetic retinopathy, macular degeneration, retinal vein occlusions, retinopathy of prematurity, retinal artery microaneurysm, hypertensive retinopathy, preeclampsia, atherosclerosis, vasculitis, blood dyscrasia, a systemic infection, radiation exposure, lupus, AIDs, age-related macular degeneration, or any other disease associated with retinopathy.

4. The method of claim 1, wherein the retinal vascular feature comprises one or more features comprising a vessel orientation ranging from 0° to 180°, a retinal sector, or a retinal layer.

5. The method of claim 4, wherein the retinal sector comprises 8 equal sections of a macula.

6. The method of claim 4, wherein the retinal sector comprises at least a temporal-inferior sector, an inferior-temporal sector, an inferior-nasal sector, a nasal-inferior sector, a nasal-superior sector, a superior-nasal sector, a superior-temporal sector, or a temporal-superior sector.

7. The method of claim 4, wherein the retinal layer is selected from the group comprising a full-projection layer, a superficial vascular plexus, an intermediate capillary plexus, a deep capillary plexus, a superficial vascular complex, and a deep vascular complex.

8. The method of claim 4, wherein the vessel of a diabetic retinopathy patient aligned between 0°-39° is about 40%-80% different compared to a normal patient in a superficial vascular complex or a deep vascular complex of an inferior-nasal sector;

wherein the vessel of the diabetic retinopathy patient aligned between 40°-79° is about 25%-40% different compared to a normal patient in the superficial vascular complex or the deep vascular complex of the inferior-nasal sector;

wherein the vessel of the diabetic retinopathy patient aligned between 80°-119° is about 0%-20% different compared to a normal patient in the superficial vascular complex or the deep vascular complex of the inferior-nasal sector; or wherein the vessel of the diabetic retinopathy patient aligned between 120°-149° is about 15%-50% different compared to a normal patient in the superficial vascular complex or the deep vascular complex of the inferior-nasal sector.

9. The method of claim 4, wherein the vessel of the DR patient aligned between 150°-180° is about 40%-80% different compared to a normal patient in a superficial vascular complex or a deep vascular complex of an inferior-nasal sector.

10. The method of claim 1, wherein the imaging modality comprises an optical coherence tomography angiography imaging, fluorescent angiography imaging, indocyanine green angiography imaging, or color fundus photography imaging.

11. The method of claim 1, wherein the multi-dimensional quantification further comprises a preferred vessel orientation, a vessel anisotropy, and a vessel area.

12. The method of claim 1, wherein the vascular orientation pattern captures local variations in the vessel orientation.

13. The method of claim 1, wherein the normal range of the diabetic retinopathy patient is between 0%-20% different compared to a normal patient;

wherein the mildly abnormal range of the diabetic retinopathy patient is between 20%-40% different compared to a normal patient; or wherein the severely abnormal range of the diabetic retinopathy patient is more than 40% different compared to a normal patient.

14. The method of claim 1, wherein an area under the retinal vascular orientation curve indicates the vessel area density.

15. The method of claim 1, wherein the patient in the treatment range receives a treatment corresponding to the retinal vascular disease.

16. The method of claim 15, wherein the treatment is anti-vascular endothelial growth factors, laser, and/or gene therapy.

17. The method of claim 1, wherein the patient is screened and treated for an ocular or retinal vascular disease progression, wherein the disease progression is indicated by a change in a preferred vessel orientation.

18. The method of claim 17, wherein the change in the preferred vessel orientation is a 10% or more increase compared to a normal patient in a superficial vascular complex or a deep vascular complex of the patient.

19. The method of claim 1, wherein the first and second sets of quantification metrics are used by a trained machine learning or neural network to output an indication of a presence or non-presence of ocular or retinal vascular disease, wherein the trained machine learning or neural network was trained using orientation vectors at each pixel, or the set thereof, of pre-defined regions of a training data set comprising ocular or retinal vascular images or objects and labels for the ocular or retinal vascular disease.

20. The method of claim 1, wherein the set of orientation vectors are determined by:

generating a Hessian matrix of intensity values of the ocular or retinal vascular image or object; and determining eigenvectors corresponding to the smallest eigenvalue in magnitude of the Hessian matrix.

21. The method of claim 1, wherein quantification metrics are generated from a set of 8 pre-defined retinal sectors centered at an identified landmark corresponding to the macula.

22. The method of claim 1, wherein the first quantification metrics includes an aggregation or sum of a number of orientation vectors in a pre-defined angle or angular range.

23. The method of claim 1, wherein the ocular or retinal vascular data comprises 2D ocular or retinal vascular data, 3D ocular or retinal vascular data, or time-dependent ocular or retinal vascular data.

24. A system comprising:

a processor; and a memory having instructions stored thereon, wherein execution of the instructions by the processor causes the processor to:

receive a data set comprising ocular or retinal vascular image or object;

determine a set of orientation vectors at each pixel, or a set of pixels, of a set of pre-defined regions of the ocular or retinal vascular image or object, including a first region and a second region;

determine a set of first quantification metrics from the set of orientation vectors for the first region; and determine a set of second quantification metrics from the set of orientation vectors for the second region;

wherein the first and second sets of quantification metrics are employed in a diagnosis or a treatment of an ocular or retinal vascular disease, wherein the system is employed in a set of steps comprising:

extracting a retinal vascular feature from a set of images acquired by an imaging modality and obtained from the patient to provide to the system;

carrying out a multi-dimensional quantification comprising layer- and sector-based regions of interest via the system to generate a collection of vascular orientation pattern curves;

analyzing the vascular orientation pattern curves via a trained AI model of the system;

placing the patient into a group based on the analysis of the vascular orientation pattern curve of the patient, wherein said groups comprise: i. a normal range, ii. mildly abnormal range, and iii. a severely abnormal range; and selecting the patient from group ii for further monitoring, and selecting the patient from group iii for treatment.

25. A non-transitory computer-readable medium having instructions stored thereon, wherein execution of the instructions by the processor causes the processor to:

receive a data set comprising ocular or retinal vascular image or object;

determine a set of orientation vectors at each pixel, or a set of pixels, of a set of pre-defined regions of the ocular or retinal vascular image or object, including a first region and a second region;

determine a set of first quantification metrics from the set of orientation vectors for the first region; and determine a set of second quantification metrics from the set of orientation vectors for the second region;

wherein the first and second sets of quantification metrics are employed in a diagnosis or a treatment of an ocular or retinal vascular disease wherein the computer-readable medium is employed to execute a set of steps when executed by the processor comprising:

extracting a retinal vascular feature from a set of
images acquired by an imaging modality and
obtained from the patient to provide to the system;

carrying out a multi-dimensional quantification com-
prising layer- and sector-based regions of interest via
the system to generate a collection of vascular ori-
entation pattern curves;

analyzing the vascular orientation pattern curves via a
trained AI model of the system;

placing the patient into a group based on the analysis of the vascular orientation pattern curve of the patient,
wherein said groups comprise: i. a normal range, ii.
mildly abnormal range, and iii. a severely abnormal
range; and selecting the patient from group ii for further monitoring, and selecting the patient from group iii for
treatment.

<p style="text-align:center">* * * * *</p>